(12) United States Patent
Takahashi et al.

(10) Patent No.: US 12,059,462 B2
(45) Date of Patent: Aug. 13, 2024

(54) COMPOSITION CONTAINING INFLUENZA VACCINE

(71) Applicants: JAPAN as represented by DIRECTOR GENERAL of National Institute of Infectious Diseases, Tokyo (JP); Sumitomo Pharma Co., Ltd., Osaka (JP)

(72) Inventors: Yoshimasa Takahashi, Tokyo (JP); Yu Adachi, Tokyo (JP); Manabu Ato, Tokyo (JP); Akihisa Fukushima, Osaka (JP)

(73) Assignees: JAPAN as represented by DIRECTOR GENERAL of National Institute of Infectious Diseases, Tokyo (JP); Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 17/262,021

(22) PCT Filed: Jul. 22, 2019

(86) PCT No.: PCT/JP2019/028674
§ 371 (c)(1),
(2) Date: Jan. 21, 2021

(87) PCT Pub. No.: WO2020/022272
PCT Pub. Date: Jan. 30, 2020

(65) Prior Publication Data
US 2021/0353737 A1    Nov. 18, 2021

(30) Foreign Application Priority Data

Jul. 23, 2018  (JP) ................................ 2018-138001
Mar. 4, 2019   (JP) ................................ 2019-038976

(51) Int. Cl.
| A61K 39/145 | (2006.01) |
| A61K 39/39  | (2006.01) |
| A61K 47/54  | (2017.01) |
| A61P 31/16  | (2006.01) |
| A61K 39/00  | (2006.01) |

(52) U.S. Cl.
CPC ............ *A61K 39/145* (2013.01); *A61K 39/39* (2013.01); *A61K 47/54* (2017.08); *A61P 31/16* (2018.01); *A61K 2039/55511* (2013.01)

(58) Field of Classification Search
None
See application file for complete search history.

(56) References Cited

U.S. PATENT DOCUMENTS

| 4,689,338 A    | 8/1987 | Gerster |
| 2010/0099870 A1* | 4/2010 | Isobe ........................ A61P 9/14 |
|                |        | 544/276 |
| 2010/0305030 A1 | 12/2010 | Couvreur et al. |
| 2012/0270255 A1 | 10/2012 | Graninger et al. |
| 2013/0209499 A1 | 8/2013  | Garcia-Sastre et al. |
| 2015/0098966 A1 | 4/2015  | Ni et al. |
| 2016/0045590 A1 | 2/2016  | Milner et al. |
| 2016/0052997 A1 | 2/2016  | Hong et al. |
| 2018/0021258 A1 | 1/2018  | Graham et al. |
| 2018/0280499 A1 | 10/2018 | Kimura et al. |
| 2018/0282334 A1 | 10/2018 | Ban et al. |
| 2019/0142930 A1 | 5/2019  | Ni et al. |
| 2019/0345231 A1 | 11/2019 | Takahashi et al. |
| 2020/0121600 A1 | 4/2020  | Fukushima |
| 2021/0008197 A1 | 1/2021  | Kimura et al. |
| 2022/0152191 A1 | 5/2022  | Takahashi et al. |

FOREIGN PATENT DOCUMENTS

| CN | 101524538      | 9/2009  |
| CN | 102939096      | 2/2013  |
| EP | 1110951        | 6/2001  |
| EP | 3679948        | 7/2020  |
| JP | 2011-506276    | 3/2011  |
| JP | 2012-507502    | 3/2012  |
| JP | 2015-520729    | 7/2015  |
| JP | 2016-516090    | 6/2016  |
| JP | 2018-501801    | 1/2018  |
| JP | 2019-043937    | 3/2019  |
| KR | 10-2011-0047193 | 5/2011 |
| KR | 10-2011-0102198 | 9/2011 |
| WO | WO 2000/012487 | 3/2000  |
| WO | WO 2005/001022 | 1/2005  |
| WO | WO 2005/018555 | 3/2005  |
| WO | WO 2008/054481 | 5/2008  |
| WO | WO 2009/067081 | 5/2009  |
| WO | WO 2010/047509 | 4/2010  |
| WO | WO 2010/048520 | 4/2010  |
| WO | WO 2010/049899 | 5/2010  |
| WO | WO 2010/093436 | 8/2010  |

(Continued)

OTHER PUBLICATIONS

Chun et al., "Universal antibodies and their applications to the quantitative determination of virtually all subtypes of the influenza A viral hemagglutinins," Vaccine, Nov. 2008, 26(48):6068-6076.

Dowling, "Recent Advances in the Discovery and Delivery of TLR7/8 Agonists as Vaccine Adjuvants," Immunohorizons, Jul. 2018, 2(6):185-197, 14 pages.

Extended European Search Report in European Appln. No. 19842246. 1, dated Mar. 21, 2022, 12 pages.

Kazaks et al., "Production and purification of chimeric HBec virus-like particles carrying influenza virus LAH domain as vaccine candidates," BMC Biotechnology, Nov. 2017, 17(1), 79, 11 pages.

Van Hoeven et al., "A Formulated TLR7/8 Agonist is a Flexible, Highly Potent and Effective Adjuvant for Pandemic Influenza Vaccines," Scientific Reports, Apr. 2017, 7(1):15 pages.

(Continued)

*Primary Examiner* — Benjamin P Blumel
(74) *Attorney, Agent, or Firm* — Fish & Richardson P.C.

(57) ABSTRACT

The present invention provides a composition comprising a universal influenza vaccine antigen and a vaccine adjuvant.

Figure 1:
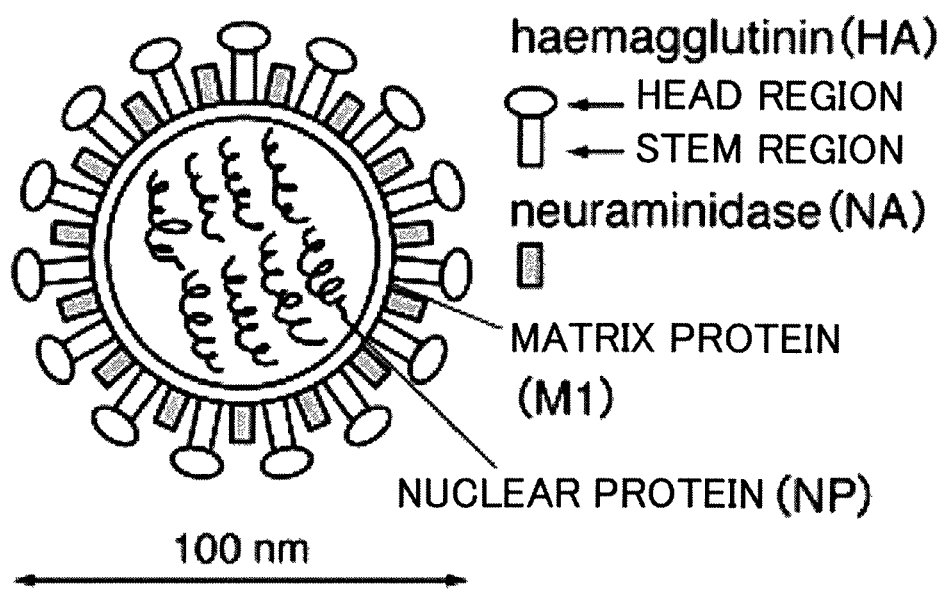

19 Claims, 15 Drawing Sheets
Specification includes a Sequence Listing.

(56) References Cited

FOREIGN PATENT DOCUMENTS

| WO | WO 2010/133885 | 11/2010 |
|---|---|---|
| WO | WO 2011/017611 | 2/2011 |
| WO | WO 2011/123495 | 10/2011 |
| WO | WO 2011/139348 | 11/2011 |
| WO | WO 2012/024284 | 2/2012 |
| WO | WO 2012/066335 | 5/2012 |
| WO | WO 2012/066336 | 5/2012 |
| WO | WO 2012/067268 | 5/2012 |
| WO | WO 2012/067269 | 5/2012 |
| WO | WO 2012/145386 | 10/2012 |
| WO | WO 2013/172479 | 11/2013 |
| WO | WO 2013/173256 | 11/2013 |
| WO | WO 2016/109792 | 7/2016 |
| WO | WO 2017/056494 | 4/2017 |
| WO | WO 2017/061532 | 4/2017 |
| WO | WO 2018/181420 | 10/2018 |
| WO | WO 2020/138217 | 7/2020 |
| WO | WO 2020/179797 | 9/2020 |

OTHER PUBLICATIONS

White et al., "Anti-peptide antibodies detect steps in a protein conformational change: low-pH activation of the influenza virus hemagglutinin," The Journal Of Cell Biology, Dec. 1987, 105(6):2887-2896.
Zheng et al., "Influenza H7N9 LAH-HBc virus-like particle vaccine with adjuvant protects mice against homologous and heterologous influenza viruses," Vaccine, Nov. 2016, 34(51):6464-6471.
Zhou et al., "Improving influenza vaccines: challenges to effective implementation," Current Opinion in Immunology, Apr. 2018, 53:88-95.
[No Author Listed], "The 16th Awaji International Forum on Infection and Immunity Program at a Glance," Poster, Presented at The 16th Awaji International Forum on Infection and Immunity, Japan, Sep. 5-8, 2017, 1 page.
[No Author Listed], "U.S.-Japan Cooperative Medical Sciences Program (USJCMSP) 22nd International Conference on Emerging Infectious Diseases in the Pacific Rim," Faculty of Medicine, Chulalongkorn University, Bangkok, Thailand, Feb. 24-27, 2020, 8 pages.
Adachi et al., "Exposure of an occluded hemagglutinin epitope drives selection of a class of cross-protective influenza antibodies," Nature Communications, Aug. 2019, 10(3883):1-13.
Arias et al., "Squalene Based Nanocomposites: A New Platform for the Design of Multifunctional Pharmaceutical Theragnostics," ACS Nano, Jan. 2011, 5(2):1513-1521.
Byrd-Leotis et al., "Influenza Hemagglutinin (HA) Stem Region Mutations That Stabilize or Destabilize the Structure of Multiple HA Subtypes," Journal of Virology, Apr. 2015, 89(8):4504-4516.
Chan et al., "Synthesis and Immunological Characterization of Toll-Like Receptor 7 Agonistic Conjugates," Bioconjugate Chem., May 2009, 20(6):1194-1200.
DiLillo et al., "Broadly neutralizing hemagglutinin stalk-specific antibodies require FcγR interactions for protection against influenza virus in vivo," Nat. Medicine, Feb. 2014, 20:143-151, 11 pages.
Doms et al., "Quaternary Structure of Influenza Virus Hemagglutinin after Acid Treatment," Journal of Virology, Dec. 1986, 60(3):833-839.
Fox, "Squalene Emulsions for Parenteral Vaccine and Drug Delivery," Molecules, Sep. 2009, 14(9):3286-3312.
Goff et al., "Synthetic Toll-Like Receptor 4 (TLR4) and TLR7 Ligands as Influenza Virus Vaccine Adjuvants Induce Rapid, Sustained, and Broadly Protective Responses," Journal of Virology, Mar. 2015, 89(6):3221-3235.
Impagliazzo et al., "A stable trimeric influenza hemagglutinin stem as a broadly protective immunogen," Science, Sep. 2015, 349(6254):1301-1306, 12 pages.
Iwasaki et al., "Toll-like receptor control of the adaptive immune responses," Nat. Immunol., Oct. 2004, 5:987-995.

Kostolansky et al., "Inhibition of influenza virus haemolytic and haemagglutination activities by monoclonal antibodies to haemagglutinin glycopolypeptides HA1 and HA2," Acta Virologica, Dec. 1989, 33(6):504-512, 7 pages.
Krammer, "Novel universal influenza virus vaccine approaches," Current Opinion in Virology, Apr. 2016, 17:95-103.
National Institute of Infectious Diseases, "Biological Products Standards," Mar. 30, 2004, Ministerial Notification No. 155 of Ministry of Health, Labor and Welfare, most recent revision Nov. 30, 2018, Ministerial Notification No. 409, retrieved from URL <https://www.niid.go.jp/niid/images/qa/seibutuki/seibutsuki_japanese/20210521.pdf>, English version retrieved from URL <https://www.niid.go.jp/niid/images/qa/seibutuki/MRBP_english/mrbp_2006.pdf>, 662 pages (with English version).
O'Hagan et al., "The mechanism of action of MF59—An innately attractive adjuvant formulation," Vaccine, Jun. 2012, 30:4341-4348.
Ott et al., "The Adjuvant MF59: A 10-Year Perspective," Methods in Molecular Medicine, 2000, 42:211-228.
PCT International Preliminary Report on Patentability in International Appln. No. PCT/JP2019/028674, dated Feb. 4, 2021, 17 pages (with English translation).
PCT International Search Report and Written Opinion in International Appln. No. PCT/JP2019/028674, dated Oct. 15, 2019, 22 pages (with English translation).
Quan et al., "Immunogenicity of low-pH treated whole viral influenza vaccine," Virology, Aug. 2011, 417:196-202.
Smirnov et al., "Vaccine adjuvant activity of 3M-052: An imidazoquinoline designed for local activity without systemic cytokine induction," Vaccine, Jul. 2011, 29(33):5434-5442.
Steinhagen et al., "TLR-based immune adjuvants," Vaccine, Apr. 2011, 29(17):3341-3355.
Takahashi, "Broadly Protective Antibodies and Vaccines," Presentation Abstract from 22nd International Conference on Emerging Infectious Diseases in the Pacific Rim, Bangkok, Thailand, Feb. 24, 2020, 2 pages.
Takahashi, "Broadly protective antibodies and vaccines," Presented at 22nd International Conference on Emerging Infectious Diseases in the Pacific Rim, Bangkok, Thailand, Feb. 24, 2020, 15 pages.
Takahashi, "Regulation of antibody breadth to mutating viruses through distinct germinal center selection," Poster, Presented at The 16th Awaji International Forum on Infection and Immunity, Japan, Sep. 5-8, 2017, 21 pages.
Tomai et al., "Resiquimod and other immune response modifiers as vaccine adjuvants," Exp. Rev. Vaccine, 2007, 6:835-847.
Valetti et al., "Peptide Conjugation: Before or After Nanoparticle Formation," Bioconjugate Chemistry, Oct. 2014, 25(11):1971-1983.
Yassine et al., "Hemagglutinin-stem nanoparticles generate heterosubtypic influenza protection," Nature Medicine, Sep. 2015, 21(9):1065-1070, 9 pages.
EP Extended European Search Report in European Appln. No. 18852584.4, dated Mar. 31, 2021, 7 pages.
Extended European Search Report in European Appln. No. 20766488.9, dated Aug. 25, 2022, 7 pages.
Garcia et al., "Dynamic Changes during Acid-Induced Activation of Influenza Hemagglutinin," Structure, Apr. 2015, 23(4):665-676, 13 pages.
International Preliminary Report on Patentability in International Appln. No. PCT/JP2020/008974, dated Sep. 16, 2021, 13 pages (with English translation).
International Search Report and Written Opinion in International Appln. No. PCT/JP2020/008974, dated Jun. 9, 2020, 16 pages (with English translation).
National Institute of Infectious Diseases, "Minimum Requirements for Biological Products," retrieved from URL <https://www.niid.go.jp/niid/images/qa/seibutuki/MRBP_english/mrbp_2006.pdf>, 2006, 339 pages (English version only).
Office Action in U.S. Appl. No. 16/292,065, dated Aug. 17, 2022, 8 pages.
Office Action in U.S. Appl. No. 16/292,065, dated Jan. 20, 2022, 8 pages.
Office Action in U.S. Appl. No. 16/292,065, dated Oct. 12, 2021, 7 pages.

(56) References Cited

OTHER PUBLICATIONS

Office Action in U.S. Appl. No. 16/292,065, dated Oct. 5, 2020, 10 pages.
Office Action in U.S. Appl. No. 17/262,021, dated Aug. 4, 2022, 8 pages.
PCT International Preliminary Report on Patentability in International Appln. No. PCT/JP2018/032537, dated Mar. 10, 2020, 9 pages (with English translation).
PCT International Search Report in International Appln. No. PCT/JP2018/032537, dated Nov. 20, 2018, 6 pages (with English translation).
PCT Written Opinion in International Appln. No. PCT/JP2018/032537, dated Nov. 20, 2018, 7 pages (with English translation).
Sanofi Pasteur, "450 Fluzone Quadrivalent," retrieved from URL <https://www.seacoastmedical.com/storefrontCommerce/forms/ProductInfo/Fluzone%20Quadrivalent%20PI.pdf>, Jun. 2013, 31 pages.
Takahashi, "Abstract: Broadly protective antibodies and vaccines," Presented at U.S.-Japan Cooperative Medical Sciences Program (USJCMSP), 22nd International Conference on Emerging Infectious Diseases in the Pacific Rim, Bangkok, Thailand, Feb. 24, 2020, 10 pages.
Takahashi, "Broadly protective antibodies and vaccines," Presented at U.S.-Japan Cooperative Medical Sciences Program (USJCMSP), 22nd International Conference on Emerging Infectious Diseases in the Pacific Rim, Bangkok, Thailand, Feb. 24, 2020, 23 pages.
Zost et al., "Immunodominance and Antigenic Variation of Influenza Virus Hemagglutinin: Implications for Design of Universal Vaccine Immunogens," The Journal of Infectious Diseases, Apr. 2019, 219(Suppl 1): S38-S45.
Notice of Allowance in U.S. Appl. No. 16/292,065, dated Dec. 8, 2022, 9 pages.
Ren et al., "Epitope-focused vaccine design against influenza A and B viruses," Curr. Opin. Immunol., Oct. 2016, 42:83-90.
Goff et al., "Adjuvants and Immunization Strategies to Induce Influenza Virus Hemagglutinin Stalk Antibodies," PLOS ONE, Nov. 2013, 8(11):e79194, 1-11.
Harrison, "Viral membrane fusion," Nat. Struct. Mol. Biol., Jul. 2008, 15(7):690-698.
Iwami Kagaku Dictionary, Saburo Nagakura et al. (ed.), Fifth Edition, Nov. 2003, Iwanami Shoten, 327, 3 pages (with partial English translation).
Kazaks et al., "Production and purification of chimeric HBc virus-like particles carrying influenza virus LAH domain as vaccine candidates," BMC Biotechnology, Nov. 2017, 17(1), 79, 11 pages.
Krammer, "The Quest for a Universal Flu Vaccine: Headless HA 2.0," Cell Host & Microbe, Oct. 2015, 18(4):395-397.
Nachbagauer et al., "A chimeric haemagglutinin-based influenza split virion vaccine adjuvanted with AS03 induces protective stalk-reactive antibodies in mice," NPJ Vaccines, Sep. 2016, 1(16015):1-10.
Nachbagauer et al., "A universal influenza virus vaccine candidate confers protection against pandemic H1N1 infection in preclinical ferret studies," NPJ Vaccines, Sep. 2017, 2(26):1-13.
Nguyen et al., "Targeting Antigens for Universal Influenza Vaccine Development," Viruses, May 2021;13(6):973, 21 pages.
Notice of Allowability in U.S. Appl. No. 16/292,065, dated Mar. 29, 2023, 8 pages.
Notice of Allowance in U.S. Appl. No. 16/292,065, dated Mar. 3, 2023, 9 pages.
Valkenburg et al., "Stalking influenza by vaccination with pre-fusion headless HA mini-stem," Scientific Reports, Mar. 2016, 6(22666):1-11.
Graves et al., "Preparation of Influenza Virus Subviral Particles Lacking the HA1 Subunit of Hemagglutinin: Unmasking of Cross-Reactive HA2 Determinants," Virology, Apr. 1983, 126(1):106-116.
U.S. Appl. No. 18/341,960, filed Jun. 27, 2023, Takahashi et al.
Chen et al., "Protection against Multiple Subtypes of Influenza Viruses by Virus-Like Particle Vaccines Based on a Hemagglutinin Conserved Epitope," Biomed Res. Int., Feb. 2015, 2015(901817), 12 pages.
Notice of Allowance in U.S. Appl. No. 16/292,065, dated Jun. 2, 2023, 9 pages.
Notice of Allowability in U.S. Appl. No. 16/292,065, dated Jun. 22, 2023, 5 pages.
Bullard et al., "Strategies Targeting Hemagglutinin as a Universal Influenza Vaccine," Vaccines, Mar. 2021, 9(3):257, 18 pages.
Xagorari et al., "Toll-Like Receptors and Viruses: Induction of Innate Antiviral Immune Responses," The Open Microbiology Journal, May 2008, 2:49-59.

* cited by examiner

COMPOSITION CONTAINING INFLUENZA VACCINE

TECHNICAL FIELD

The present invention relates to a composition comprising a vaccine adjuvant and a universal influenza vaccine antigen.

BACKGROUND ART

Component vaccines comprising virus-derived proteins or partial peptides thereof are safer than live vaccines or whole-particle inactivated vaccines. However, component vaccines tend to have low immunostimulatory efficacy. Therefore, in order to enhance the immunogenicity of the epitope and to improve the immuno-stimulating activity of the vaccines, it has been investigated for methods using an adjuvant and an antigen in combination. Adjuvants are an additive to enhance humoral and/or cellular immune responses to antigens, and Alum, saponin, and the like have been used as a vaccine adjuvant.

Recently, it has been found that Toll-like Receptor (TLR) plays an important role in the activation of innate immunity, which is one of the defense mechanisms in living organisms against microorganisms, and that monophosphoryl lipid A (MPL), oligodeoxynucleotide containing unmethylated cytidyl guanosyl (CpG) sequence (CpG ODN), etc., have immunostimulatory effects via TLR. It is said that of the known thirteen TLRs identified in human, five TLRs (TLRs 1, 2, 4, 5, 6) are involved in recognition of bacterial components, and four TLRs (TLR 3, 7, 8, 9) are involved in recognition of viral nucleic acids (Non Patent Document 1). As an agonist (activator) of TLR7 and TLR8, small molecules that mimic a single-stranded RNA of virus, which is a natural ligand, has been known. For example, synthetic compounds, such as pyrimidine compounds (Patent Documents 1 and 2) and imidazoquinoline compounds (Patent Document 3), have been reported.

Activation of TLR7 and/or TLR8 with its agonists activates dendritic cells (DC) via TLR and myeloid differentiation factor 88 (MyD 88)-dependent signaling pathway. As a result, the expression of the T cell co-stimulatory molecules (CD80, CD86, CD40) is enhanced, and inflammatory cytokines including type I interferon (especially IFNα), TNFα, IL-6 or IL-12 are produced.

In addition to the activation of DC, the TLR7 and/or TLR8 agonists (activator) are known to activate T and B cells and further stimulate NK cells to promote IFNγ production, and therefore it is expected to have a vaccine adjuvant activity. Indeed, adjuvant activity of TLR7 and/or TLR8 agonists, such as Resiquimod and Imiquimod, has been reported (Non Patent Document 2).

The following complexes of TLR7 and/or TLR 8 agonists with other substances are known: vaccine adjuvants in which fatty acids and imidazoquinoline compounds are covalently linked (Patent Documents 4, 5, 6 and Non-Patent Document 4), conjugated compounds of phospholipids and adenine compounds (Patent Documents 7, 8, and 9), conjugated compounds of fatty acids and adenine compounds (Non-Patent Document 5), conjugated compounds of fatty acid glycerides or phospholipids and adenine compounds via polyethylene glycol (Patent Document 10), conjugated compounds of squalenes and adenine compounds (Patent Document 11), and conjugated compounds of squalenes and pyrimidine compounds (Patent Document 12).

Current influenza haemagglutinin (hereinafter also abbreviated as "HA") vaccines, which are also called influenza HA split vaccines, induce an anti-HA antibody, thereby exerting a protective effect against infection. The anti-HA antibody binds to a portion of a virus called a "head region" in hemagglutinin externally exposed from a virus membrane. This region most frequently undergoes structural change in a viral strain. Therefore, in some cases, the anti-HA antibody may fail to bind to a virus which causes antigenic variation and is different from the vaccine strain, and the vaccine cannot exert the protective effect against the infection.

Recently, it has been revealed that antibodies that bind to a stem region in hemagglutinin which is less likely to cause antigenic variation (anti-stem antibody) include protective antibodies against infection (Patent Document 13). In order to efficiently induce the anti-stem antibody, a HA stem protein having a stabilized stem portion has been developed, and its clinical trial in humans has been carried out: the stem portion, which is originally unstable, has been stabilized through artificial variation in hemagglutinin or binding of linkers to hemagglutinin. However, in the practical application of the HA stem protein, there still remain problems in the improvement of immunogenicity and in the production process.

It has been reported that the ability of anti-stem antibodies to protect against infection depends not only on their antigen binding properties and antibody levels, but also strongly on the subclass of the induced IgG antibodies (Non Patent Document 3). Specifically, it has been shown that stem IgG2 antibodies are functional and cross-reactive, and vaccines that strongly induce anti-stem IgG2 antibodies are effective in protecting against a wide range of influenza infections. However, no method for effectively-enhancing the ability of the vaccines to induce the anti-stem IgG2 antibodies has been found.

PRIOR ART DOCUMENT

Patent Document

Patent Document 1: WO 00/12487
Patent Document 2: WO 2009/067081
Patent Document 3: US Patent Application Publication U.S. Pat. No. 4,689,338
Patent Document 4: WO 2005/001022
Patent Document 5: WO 2005/018555
Patent Document 6: WO 2012/024284
Patent Document 7: WO 2010/048520
Patent Document 8: WO 2011/017611
Patent Document 9: WO 2011/139348
Patent Document 10: WO 2010/093436
Patent Document 11: WO 2017-061532
Patent Document 12: WO 2017-056494
Patent Document 13: JP 2016-516090 A
Patent Document 14: WO 2016/109792

Non Patent Document

Non Patent Document 1: Iwasaki, A., Nat. Immunol. 2004, 5, 987
Non Patent Document 2: Vaccine 2011, 29, 3341•M. A. Tomai et al, Exp. Rev. Vaccine, 6, 835
Non Patent Document 3: DiLillo, D J., Nat. Medicine 2014, 20, 143
Non Patent Document 4: Vaccine. 2011 Jul. 26; 29(33): 5434-42
Non Patent Document 5: Bioconjugate Chem. 2009, 20, 1194-1200

Non Patent Document 6: Curr Opin Virol. 2016, 17, 95-103
Non Patent Document 7: Nat Med. 2015, 21, 1065-70
Non Patent Document 8: Science. 2015, 349, 1301-6

SUMMARY OF INVENTION

Technical Problem

An object of the present application is to find an influenza HA split vaccine that effectively produces an antibody that binds to a HA stem region, which is less likely to undergo antigenic variation, of an influenza virus, and to provide a method for improving the ability of the vaccine to induce an IgG2 antibody.

Solution to Problem

The present inventors have intensively studied to solve the above problems, and have found that by subjecting a current influenza HA split vaccine to an acidic treatment, the stem region of hemagglutinin is exposed to the outside, and the influenza HA split vaccine after the acidic treatment may produce a cross-reactive antibody capable of binding to LAH (long alpha helix) in the HA stem region, and thereby may serve as a universal influenza vaccine antigen. Furthermore, the present inventors have found that by adding a compound that enhances the physiological activity of TLR7 to the influenza HA split vaccine after the acidic treatment, the compound functions as a vaccine adjuvant, and the IgG2 antibody inducing ability of the vaccine is improved, and thereby have achieved the present invention.

Specifically, the present invention relates to the following.

Item 1

A composition comprising the following (1) and (2);
(1) a universal influenza vaccine antigen; and
(2) a vaccine adjuvant.

Item 2

The composition according to Item 1, wherein the universal influenza vaccine antigen is an influenza HA split vaccine antigen which produces an antibody that binds to a LAH of a HA stem region.

Item 3

The composition according to Item 2, wherein the influenza HA split vaccine antigen has a HA stem region exposed outside.

Item 4

The composition according to Item 1, wherein the universal influenza vaccine antigen is an influenza HA split vaccine antigen wherein the HA stem region, which is exposed outside, enhances the antigenicity of the LAH of the HA stem region, and the influenza HA split vaccine is capable of producing an antibody that binds to the LAH of the HA stem region.

Item 5

The composition according to any one of Items 1 to 4, wherein the universal influenza vaccine antigen is produced by subjecting an influenza HA split vaccine to an acidic treatment.

Item 6

The composition according to any one of Items 1 to 5, wherein the universal influenza vaccine antigen is produced by subjecting an influenza HA split vaccine which has not undergone a formalin treatment to an acidic treatment.

Item 7

The composition according to any one of Items 1 to 6, wherein the universal influenza vaccine antigen is produced by a production process including: subjecting an influenza HA split vaccine to an acidic treatment; and thereafter, subjecting the influenza HA split vaccine to a formalin treatment.

Item 8

The composition according to any one of Items 1 to 7, wherein the universal influenza vaccine antigen is produced by subjecting an influenza HA split vaccine of a single HA subtype to an acidic treatment.

Item 9

The composition of according to any one of Items 1 to 7, wherein the universal influenza vaccine antigen is a vaccine antigen comprising two or more kinds of influenza HA split vaccine antigens each of which is produced by subjecting an influenza HA split vaccine of a single HA subtype to an acidic treatment.

Item 10

The composition of any one of Items 1 to 9, wherein the vaccine adjuvant is a substance which enhances the physiological activity of TLR.

Item 11

The composition of any one of Items 1 to 10, wherein the vaccine adjuvant is a substance which enhances the physiological activity of one or more TLRs selected from the group consisting of TLR7, TLR8, and TLR9.

Item 12

The composition of any one of Items 1 to 11, wherein the vaccine adjuvant is a substance which enhances the physiological activity of at least TLR7.

Item 13

The composition of any one of Items 1 to 12, wherein the vaccine adjuvant is a substance which enhances the physiological activity of at least TLR8.

Item 14

The composition of any one of Items 1 to 13, wherein the vaccine adjuvant is a substance which enhances the physiological activity of at least TLR9.

Item 15

The composition according to Items 11 or 12, wherein the substance which enhances the physiological activity of TLR7 is a low molecular weight compound which enhances the physiological activity of TLR7, or a conjugated compound in which a low molecular weight compound which enhances the physiological activity of TLR7 and a lipid are chemically linked via a spacer.

Item 16

The composition of Item 15, wherein the low molecular weight compound which enhances the physiological activity of TLR7 or the low molecular weight compound which enhances the physiological activity of TLR7 comprised in the conjugated compound has a molecular weight of 200 to 600 and has an adenine skeleton, a pyrimidine skeleton, an imidazoquinoline skeleton, an imidazopyridine skeleton, or a quinazoline skeleton.

Item 17

The composition of Item 16, wherein the low molecular weight compound which enhances the physiological activity of TLR7 or the low molecular weight compound which enhances the physiological activity of TLR7 comprised in the conjugated compound has a pyrimidine skeleton, an adenine skeleton, or an imidazoquinoline skeleton.

Item 18

The composition of any one of Items 15 to 17, wherein the lipid is a lipid derived from squalene or squalane.

Item 19

The composition according to any one of Items 15 to 18, wherein the compound which enhances the physiological activity of TLR7 is a conjugated compound in which a low molecular weight compound having an adenine skeleton and a lipid derived from squalene or squalane are chemically linked via a spacer or a pharmaceutically acceptable salt thereof.

Item 20

The composition according to any one of Items 15 to 18, wherein the compound which enhances the physiological activity of TLR7 is a conjugated compound in which a low molecular weight compound having a pyrimidine skeleton and a lipid derived from squalene or squalane are chemically linked via a spacer or a pharmaceutically acceptable salt thereof.

Item 21

The composition according to any one of Items 15 to 18 and 20, wherein the compound which enhances the physiological activity of TLR7 is a compound represented by Formula (1) or a pharmaceutically acceptable salt thereof:

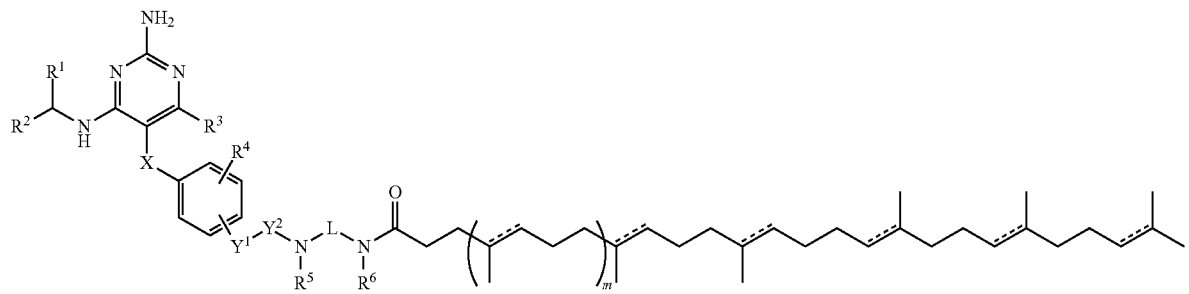

(1)

wherein

X represents methylene, $R^1$ represents a hydrogen atom or an alkyl group having 1 to 3 carbon atoms which may be substituted with hydroxy group, $R^2$ represents a hydrogen atom or an alkyl group having 1 to 6 carbon atoms, $R^3$ represents an alkyl group having 1 to 3 carbon atoms, $R^4$ represents a hydrogen atom, a halogen atom, a hydroxy group, an alkyl group having 1 to 3 carbon atoms, or an alkoxy group having 1 to 3 carbon atoms, $Y^1$ represents a single bond or methylene, $Y^2$ represents a single bond or —C(—O—)—, L represents a straight chain alkylene having 2 or 3 carbon atoms, $R^5$ and $R^6$ independently represent a hydrogen atom or an alkyl group having 1 to 3 carbon atoms, or $R^5$ and $R^6$ are taken together to form a substituted or unsubstituted 5- to 8-membered nitrogen-containing saturated heterocycle, provided that when the 5- to 8-membered nitrogen-containing saturated heterocycle is substituted, it is substituted with the same or different 1 to 4 substituents selected from hydroxy group and halogen atom, and m represents 0 or 1, ------ are all double bonds.

Item 22

The composition according to any one of Items 15 to 18, 20 and 21, wherein the conjugated compound is:
(4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;
(4E,8E,12E,16E,20E)-1-(4-{4-[(2-amino-4-{[(2S)-1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one;
(4E,8E,12E,16E,20E)-1-(4-{4-[(2-amino-4-{[(2S)-1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one;
4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide;
4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide; or
a pharmaceutically acceptable salt thereof.

Item 23

The composition according to any one of Items 15 to 18 and 20 to 22, wherein the compound which enhances the physiological activity of TLR7 is:
(4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;
4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; or
a pharmaceutically acceptable salt thereof.

Item 24

An influenza vaccine comprising the composition according to any one of Items 1 to 23.

Item 25

A method for preventing influenza comprising administering to a warm-blooded animal in need thereof a prophylactically effective amount of the composition according to any one of Items 1 to 23.

Item 26

A method for preventing influenza comprising administering to a warm-blooded animal in need thereof a prophylactically effective amount of a universal influenza vaccine antigen and a prophylactically effective amount of a vaccine adjuvant (for example, a substance which enhances the physiological activity of TLR7).

Item 27

A kit for preventing influenza comprising a universal influenza vaccine antigen, and a vaccine adjuvant (for example, a substance which enhances the physiological activity of TLR7).

Item 28

A vaccine adjuvant (for example, a substance which enhances the physiological activity of TLR7) for use in the prevention of influenza in combination with a universal influenza vaccine antigen.

Item 29

A universal influenza vaccine antigen for use in the prevention of influenza in combination with a vaccine adjuvant (for example, a substance which enhances the physiological activity of TLR7).

Item 30

Use of a vaccine adjuvant (for example, a substance which enhances the physiological activity of TLR7) in the manufacture of a composition for preventing influenza comprising a universal influenza vaccine antigen.

Item 31

Use of a universal influenza vaccine antigen in the manufacture of a composition for preventing influenza comprising a vaccine adjuvant (for example, a substance which enhances the physiological activity of TLR7).

Item 32

The method according to Item 25 or 26, the kit according to Item 27, the vaccine adjuvant according to Item 28, or the antigen according to Item 29, wherein the universal influenza vaccine antigen and the vaccine adjuvant (for example, a substance which enhances the physiological activity of TLR7) are administered simultaneously or separately.

Item 32-1

The method according to Item 25 or 26, the kit according to Item 27, the vaccine adjuvant according to Item 28, or the antigen according to Item 29, wherein the universal influenza vaccine antigen is administered prior to, after, or concurrently with the administration of the vaccine adjuvant (for example, a substance which enhances the physiological activity of TLR7).

Item 33

A method for producing a composition comprising an influenza HA split vaccine antigen and a vaccine adjuvant (for example, a substance which enhances the physiological activity of TLR7), comprising the following steps:
a) producing an influenza HA split vaccine antigen which produces an antibody that binds to a LAH of a HA stem region by subjecting an influenza HA split vaccine which has not undergone a formalin treatment to an acidic treatment; and
b) mixing the vaccine antigen obtained in step a) with the vaccine adjuvant.

Item 34

A method for producing a composition comprising an influenza HA split vaccine antigen and a vaccine adjuvant (for example, a substance which enhances the physiological activity of TLR7), comprising the following steps:

a) subjecting an influenza HA split vaccine to an acidic treatment,
b) thereafter, conducting a formalin treatment to obtain an influenza HA split vaccine antigen which produces an antibody that binds to a LAH of a HA stem region; and
c) mixing the vaccine antigen obtained in step b) with the vaccine adjuvant.

Item 35

A method for producing a kit comprising an influenza HA split vaccine antigen and a vaccine adjuvant (for example, a substance which enhances the physiological activity of TLR7), comprising the following steps:
a) producing an influenza HA split vaccine antigen which produces an antibody that binds to a LAH of a HA stem region by subjecting an influenza HA split vaccine which has not undergone a formalin treatment to an acidic treatment; and
b) combining the vaccine obtained in step a) with the vaccine adjuvant to form a kit.

Item 36

A method for producing a kit comprising an influenza HA split vaccine antigen and a vaccine adjuvant (for example, a substance which enhances the physiological activity of TLR7), comprising the following steps:
a) subjecting an influenza HA split vaccine to an acidic treatment,
b) thereafter, conducting a formalin treatment to obtain an influenza HA split vaccine antigen which produces an antibody that binds to a LAH of a HA stem region; and
c) combining the vaccine obtained in step b) with the vaccine adjuvant to form a kit.

Effect of the Invention

According to the present invention, a universal influenza vaccine antigen is provided and its vaccine activity can be further improved by adding a vaccine adjuvant.

BRIEF DESCRIPTION OF DRAWINGS

FIG. 1 is a schematic diagram illustrating an influenza virus.

FIG. 2 is a graph showing an increase in the titer of an anti-LAH antibody in sera of mice inoculated with a membrane fusion-type H3N2 HA split vaccine.

FIG. 3 is a graph showing an improvement in the cross-protective capacity of mice inoculated with the membrane fusion-type H3N2 HA split vaccine against an antigenic variant.

FIG. 4 is a graph showing an increase in the titer of an anti-LAH antibody in sera of mice inoculated with a membrane fusion-type H1N1 HA split vaccine.

FIG. 5 is a graph showing an improvement in the cross-protective capacity of mice inoculated with the membrane fusion-type H1N1 HA split vaccine against an antigenic variant.

FIG. 6 shows graphs each indicating that a LAH binding monoclonal antibody binds more strongly to a membrane fusion-type HA split vaccine than to a current HA split vaccine.

FIG. 7 shows graphs each showing the cross-reactive IgG2c-inducing activity of membrane fusion-type HA split vaccines supplemented with A-1, A-2, or CpG.

FIG. 8 shows graphs each showing the cross-reactive IgG1-inducing activity of the membrane fusion-type HA split vaccines supplemented with A-1, A-2, or CpG.

FIG. 9 shows graphs each showing the cross-reactive IgG2c/IgG1 ratio of the membrane fusion-type HA split vaccines supplemented with A-1, A-2, or CpG.

FIG. 10 shows graphs each showing the cross-reactive IgG2c-inducing activity of membrane fusion-type HA split vaccines supplemented with A-1, A-3, or AddaVax™.

FIG. 11 shows graphs each showing the cross-reactive IgG1-inducing activity of the membrane fusion-type HA split vaccines supplemented with A-1, A-3, or AddaVax™.

FIG. 12 shows graphs each showing the cross-reactive IgG2c/IgG1 ratio of the membrane fusion-type HA split vaccines supplemented with A-1, A-3, or AddaVax™.

FIG. 13 is a graph showing the cross-protective capacity of mice inoculated with the membrane fusion-type H3N2 HA split vaccines supplemented with A-1, A-3, or AddaVax™ against an antigenic variant.

FIG. 14 is a graph showing the suppressive effect of the membrane fusion-type H3N2 HA split vaccines supplemented with A-1, A-3, or AddaVax™ on mice weight loss due to antigenic variant infection.

FIG. 15 shows graphs each indicating that the LAH binding monoclonal antibody strongly binds to a membrane fusion-type HA split vaccine that has been subjected to a formalin treatment after an acidic treatment.

FIG. 16 is a graph showing an increase in the titer of an anti-LAH antibody in sera of mice inoculated with membrane fusion-type H3N2 HA split vaccines ((Pre-fix) and (Post-fix)).

FIG. 17 shows graphs each showing the cross-reactive IgG2c-inducing activity of the membrane fusion-type HA split vaccines supplemented with A-1, A-3, or AddaVax™.

FIG. 18 shows graphs each showing the cross-reactive IgG1-inducing activity of the membrane fusion-type HA split vaccines supplemented with A-1, A-3, or AddaVax™.

FIG. 19 shows graphs each showing the cross-reactive IgG2c/IgG1 ratio of the membrane fusion-type HA split vaccines supplemented with A-1, A-3, or AddaVax™.

FIG. 20 is a graph showing the cross-protective capacity of mice inoculated with the membrane fusion-type H1N1 HA split vaccines supplemented with A-1, A-3, or AddaVax™ against an antigenic variant.

FIG. 21 is a graph showing the suppressive effect of the membrane fusion-type H1N1 HA split vaccines supplemented with A-1, A-3, or AddaVax™ on mice weight loss due to antigenic variant infection.

DESCRIPTION OF EMBODIMENTS

Embodiments of the present invention will be described in detail below. The embodiments are intended to facilitate understanding of the principle of the present invention, and the scope of the invention is not limited to the following embodiments. Other embodiments, in which the configuration of the following embodiments has been appropriately replaced by those skilled in the art, are also encompassed in the scope of the present invention.

As used herein, the term "vaccine adjuvant" means a substance having an immune-enhancing effect or a preparation containing the same, which enhances the immunogenicity of an antigen by being added to the antigen.

Vaccine adjuvants herein include alum, emulsions (for example, Freund's adjuvant, MF59(Registered trademark), AddaVax™, AS03, etc.), substances that enhance the physiological activity of NOD receptors, substances that enhance the physiological activity of RIG-I receptors, substances that enhance the physiological activity of C-type lectin receptors, substances that enhance the physiological activity of cytosolic DNA receptors, substances that enhance the physiological activity of STING, substances that enhance the physiological activity of TLR, and the like.

Vaccine adjuvants herein preferably include substances that enhance the physiological activity of TLR.

As used herein, a substance which enhances the physiological activity of TLR refers to a TLR agonist having a TLR receptor agonist activity, and is not particularly limited as long as the substance enhances the function of the TLR receptor(s).

Examples of the substances which enhance the physiological activity of TLR as used herein include monophosphoryl lipid A and derivatives thereof, adenine compounds, pyrimidine compounds, imidazoquinoline compounds, benzapine compounds, imidazopyridine compounds, quinazoline compounds, guanine compounds, dihydropteridine compounds, CpG ODN, and the like.

The substances which enhance the physiological activity of TLR as used herein preferably include substances which enhance the physiological activity of one or more TLRs selected from the group consisting of TLR7, TLR8 and TLR9, and more preferably include substances which enhance the physiological activity of at least TLR7.

As used herein, a substance which enhances the physiological activity of TLR7 refers to a TLR7 agonist having a TLR7 receptor agonist activity, and is not particularly limited as long as the substance enhances the function of the TLR7 receptor.

As used herein, a substance which enhances the physiological activity of TLR8 refers to a TLR8 agonist having a TLR8 receptor agonist activity, and is not particularly limited as long as the substance enhances the function of the TLR8 receptor.

As used herein, a substance which enhances the physiological activity of TLR9 refers to a TLR9 agonist having a TLR9 receptor agonist activity, and is not particularly limited as long as the substance enhances the function of the TLR9 receptor.

Examples of the substances which enhance the physiological activity of TLR7 herein include substances which enhance the physiological activity of TLR7 or substances which enhance the physiological activity of TLR7 and TLR8.

The substances which enhance the physiological activity of TLR7 as used herein preferably include TLR7 selective agonists. As used herein, the term "TLR7 selective" means that the TLR, other than TLR7, receptor agonist activity is weaker than the TLR7 receptor agonist activity, and includes, for example, the case where the TLR7 receptor agonist activity is stronger than the TLR8 receptor agonist activity (TLR8's endogenous ligand is a single chain RNA), more specifically, the case where the TLR7 receptor agonist activity (EC 50 value) is 10 times or more of the TLR8 receptor agonist activity.

Examples of substances which enhance the physiological activity of TLR7 herein include low molecular weight compounds which enhance the physiological activity of TLR7, and conjugated compounds in which a low molecular weight compound(s) which enhances the physiological activity of TLR7 and a lipid(s) are chemically linked via a spacer(s).

Specific examples of the low molecular weight compounds which enhance the physiological activity of TLR7 herein include those having a molecular weight of 200 to 600, preferably a molecular weight of 250 to 500, and more preferably a molecular weight of 300 to 500.

The low molecular weight compounds which enhance the physiological activity of TLR7 herein preferably include compounds having an adenine skeleton(s), a pyrimidine skeleton(s), imidazoquinoline skeleton(s), an imidazopyridine skeleton(s), quinazoline skeleton(s), a guanine skeleton(s), or a dihydropteridine skeleton(s), and more preferably include compounds having an adenine skeleton(s), a pyrimidine skeleton(s), an imidazoquinoline skeleton(s).

Examples of compounds having an adenine skeleton(s) include compounds having a 4-amino-8-oxo-purine (8-oxoadenine) skeleton, such as compounds having a 4-amino-8-oxo-purine skeleton in which the 9-position is substituted with an alkyl group (for example, straight chain alkyl group having 1 to 6 carbon atoms) which may be substituted with 5 to 6 membered aromatic carbocyclic ring, 5 to 6 membered aromatic heterocyclic ring or 4 to 7 membered aliphatic nitrogen-containing heterocyclic ring. The specific examples include compounds described in MedChemComm 2011, 2, 185, such as GSK-2245035 [6-amino-2-{[(1S)-1-methylbutyl]oxy}-9-[5-(1-piperidinyl)pentyl]-7,9-dihydro-8H-purine-8-one], PF-4171455 [4-amino-1-benzyl-6-trifluoromethyl-1,3-dihydroimidazo[4,5-c]pyridine-2-one] and the like, and compounds described in WO 98/01448, WO 99/28321, WO 02/085905, WO 2008/114008, WO 2008/114819, WO 2008/114817, WO 2008/114006, WO 2010/018131, WO 2010/018134, WO 2008/101867, WO 2010/018133, WO 2009/005687, WO 2012/080730 and the like.

The compounds having an adenine skeleton(s) preferably include the following compounds or pharmaceutically acceptable salts thereof:

6-amino-9-({6-[2-(dimethylamino)ethoxy]pyridin-3-yl}methyl)-2-ethoxy-7,9-dihydro-8H-purine-8-one;
6-amino-2-(butylamino)-9-({6-[2-(dimethylamino)ethoxy]pyridin-3-yl}methyl)-7,9-dihydro-8H-purine-8-one;
N-(4-{[6-amino-2-(butylamino)-8-oxo-7,8-dihydro-9H-purin-9-yl]methyl}benzoyl)glycine;
methyl (3-{[[3-(6-amino-2-butoxy-8-oxo-7,8-dihydro-9H-purin-9-yl)propyl](3-morpholin-4-ylpropyl)amino]methyl}phenyl)acetate; or
methyl (4-{[[3-(6-amino-2-butoxy-8-oxo-7,8-dihydro-9H-purin-9-yl)propyl](3-piperidin-1-ylpropyl)amino]methyl}phenyl)acetate.

Examples of compounds having a pyrimidine skeleton(s) include compounds having a 2,4-diaminopyrimidine skeleton, such as 2,4-diaminopyrimidine in which the 6-position may optionally be substituted with an alkyl group or the like and the 5-position is substituted with an alkyl group (for example, a straight chain alkyl group having 1 to 6 carbon atoms) which may be substituted with 5 to 6 membered aromatic carbocyclic ring, 5 to 6 membered aromatic heterocyclic ring, or 4 to 7 membered aliphatic nitrogen-containing heterocyclic ring. More specific examples of the compounds include compounds described in WO 00/12487, WO 2010/133885, WO 2013/172479 or WO 2012/136834.

Examples of compounds having an imidazoquinoline skeleton(s) include compounds having a 4-amino-1H-imidazo[4,5-c]quinoline skeleton, such as Imiquimod, resiquimod or 852A[N-[4-(4-amino-2-ethyl-1H-imidazo[4,5-c]quinolin-1-yl)butyl]methanesulfonamide], such as 4-amino-1H[4,5-c]quinoline in which the 1-position is substituted with a C1-6alkyl group or a C1-6alkoxy group and the 2-position is substituted with a C1-6alkyl group or a C1-6alkoxy group. More specific examples of the compounds include compounds described in WO 2010/48520, WO 2008/135791, U.S. Pat. Nos. 4,689,338, 4,698,348, or WO 2007/030777. Preferable examples of compounds having an imidazoquinoline skeleton(s) include Imiquimod.

Examples of compounds having an imidazopyridine skeleton(s) include compounds having a 4-amino-1,3-dihydro-2H-imidazo[4,5-c]pyridine-2-one skeleton, such as compounds having a 4-amino-1,3-dihydro-2H-imidazo[4,5-c]pyridine-2-one skeleton in which the 6-position or the 7-position is substituted with a C1-6alkyl group or a C1-6alkoxy group, each of which may optionally substituted with halogen atom, and the 1-position is substituted with an alkyl group (for example, a straight chain alkyl group having 1 to 4 carbon atoms) optionally substituted with 5 to 6 membered aromatic carbocyclic ring, 5 to 6 membered aromatic heterocyclic ring or 4 to 7 membered aliphatic nitrogen-containing heterocyclic ring. More specific examples of the compounds include compounds described in WO 2007/93901 and PF-4171455[4-amino-1-benzyl-6-(trifluoromethyl)-1,3-dihydro-2H-imidazo[4,5-c]pyridine-2-one].

Examples of compounds having a quinazoline skeleton(s) include derivatives having a 2,4-diaminoquinazoline skeleton, such as compounds having a 2,4-diaminoquinazoline skeleton in which the 4-position is substituted with an alkyl group (for example, a straight or branched chain alkyl group having 1 to 8 carbon atoms) optionally substituted with hydroxyl group, halogen atom and the like. Specific examples include compounds described in WO 2012/156498 or WO 2014/76221.

Examples of compounds having a guanine skeleton(s) include compounds having a 2-amino-6-oxopurine skeleton, and specifically, Loxoribine.

Examples of compounds having a dihydropteridine skeleton(s) include compounds having a 4-amino-7,8-dihydropteridine-6 (5H)-one skeleton, specifically vesatolimod [4-amino-2-butoxy-8-[[3-[(pyrrolidin-1-yl)methyl]phenyl]methyl]-7,8-dihydropteridine-6(5H)-one].

Other examples of low molecular weight compounds that are TLR7 agonists include Isatoribine, ANA-773, and compounds described in WO 2010/077613.

Examples of lipids in the conjugated compounds in which a low molecular weight compound(s) which enhances the physiological activity of TLR7 and a lipid(s) are chemically linked via a spacer(s) as used herein include: saturated or unsaturated fatty acids having less than 100 carbon atoms; diglycerides of saturated or unsaturated fatty acids having 10 to 30 carbon atoms and glycerin; phospholipids including phosphatidic acids in which a phosphoric acid is further bonded to a diglyceride of saturated or unsaturated fatty acids having 10 to 30 carbon atoms and glycerol; and the like. Preferably, saturated or unsaturated fatty acids having 18 to 30 carbon atoms are exemplified, and more preferably, fatty acids derived from squalene or squalane are exemplified.

Examples of the fatty acids derived from squalene include (4E,8E,12E,16E,20E)-4,8,12,17,21,25-hexamethylhexacosa-4,8,12,16,20,24-hexaenoic acid and the like. Examples of the fatty acids derived from squalane include 4,8,12,17,21,25-hexamethylhexacosanoic acid and the like. A compound derived from squalene or squalane can be linked to a spacer to provide a conjugate compound by methods well known to those skilled in the art, as appropriate.

Examples of the parts of the low molecular weight compounds which enhance the physiological activity of TLR7 in the conjugated compounds in which a low molecular weight compound(s) which enhances the physiological activity of TLR7 and a lipid(s) are chemically linked via a spacer(s) as used herein include the aforementioned low molecular weight compounds which enhance the physiological activity of TLR7.

Examples of the conjugated compounds in which a low molecular weight compound(s) which enhances the physiological activity of TLR7 and a lipid(s) are chemically linked via a spacer(s) as used herein include vaccine adjuvants in which a fatty acid(s) and an imidazoquinoline compound(s) are covalently bonded (Patent Documents 4, 5, 6, and Non Patent Document 4), conjugate compounds of a phospholipid(s) and an adenine compound(s) (Patent Documents 7, 8, 9), conjugate compounds of a fatty acid(s) and an adenine compound(s) (Non Patent Document 5), conjugate compounds of a fatty acid glyceride(s) and an adenine compound(s) via a polyethylene glycol (Patent Document 10), conjugate compounds of a squalene(s) and an adenine compound(s) (Patent Document 11), conjugate compounds of a squalene(s) and a pyrimidine compound(s) (Patent Document 12), and the like.

Preferred examples of the conjugated compounds in which a low molecular weight compound(s) which enhances the physiological activity of TLR7 and a lipid(s) are chemically linked via a spacer(s) as used herein include conjugated compounds in which a low molecular weight compound(s) having an adenine skeleton(s) and a lipid(s) derived from squalene or squalane are chemically linked via a spacer(s), conjugated compounds in which a low molecular weight compound(s) having a pyrimidine skeleton(s) and a lipid(s) derived from squalene or squalane are chemically linked via a spacer(s), and pharmaceutically acceptable salts thereof.

Preferred examples of the conjugated compounds in which a low molecular weight compound(s) having an adenine skeleton(s) and a lipid(s) derived from squalene or squalane are chemically linked via a spacer(s) include compounds described in Patent Document 11.

Preferred examples of the conjugated compounds in which a low molecular weight compound(s) having a pyrimidine skeleton(s) and a lipid(s) derived from squalene or squalane are chemically linked via a spacer(s) include compounds described in Patent Document 12. More preferably, compounds represented by formula (1) or pharmaceutically acceptable salts thereof are exemplified.

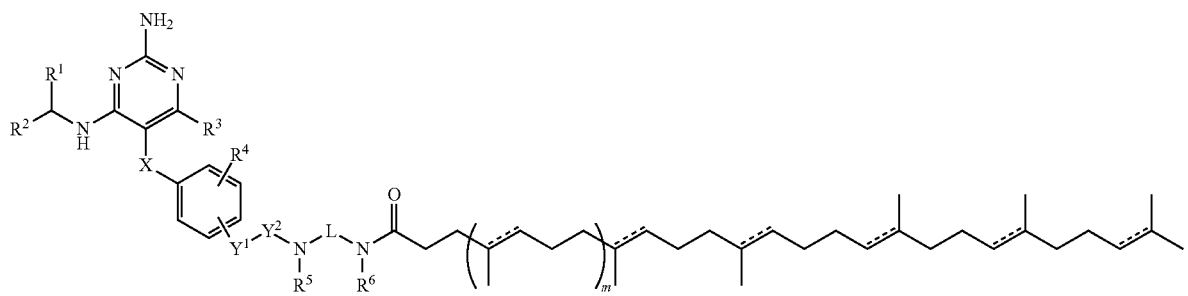

(1)

wherein
X represents methylene,
R¹ represents a hydrogen atom or an alkyl group having 1 to 3 carbon atoms which may be substituted with hydroxy group,
R² represents a hydrogen atom or an alkyl group having 1 to 6 carbon atoms,
R³ represents an alkyl group having 1 to 3 carbon atoms,
R⁴ represents a hydrogen atom, a halogen atom, a hydroxy group, an alkyl group having 1 to 3 carbon atoms, or an alkoxy group having 1 to 3 carbon atoms,
Y¹ represents a single bond or methylene,
Y² represents a single bond or —C(O)—,
L represents a straight chain alkylene having 2 or 3 carbon atoms,
R⁵ and R⁶ independently represent a hydrogen atom or an alkyl group having 1 to 3 carbon atoms, or R⁵ and R⁶ are taken together to form a substituted or unsubstituted 5- to 8-membered nitrogen-containing saturated heterocycle, provided that when the 5- to 8-membered nitrogen-containing saturated heterocycle is substituted, it is substituted with the same or different 1 to 4 substituents selected from hydroxy group and halogen atom,
m represents 0 or 1,
▬▬▬▬ are all double bonds.

The "halogen atom" includes a fluorine atom, a chlorine atom, a bromine atom, an iodine atom, and preferably includes a fluorine atom or a chlorine atom.

Examples of "a straight chain alkylene having 2 or 3 carbon atoms" include, but are not limited to, ethylene and n-propylene.

The term "an alkyl group having 1 to 3 carbon atoms" include a straight or branched alkyl group having 1 to 3 carbon atoms. Examples include, but are not limited to, methyl, ethyl, propyl, and isopropyl.

The term "an alkoxy group having 1 to 3 carbon atoms" includes a straight or branched alkoxy group having 1 to 3 carbon atoms. Examples include, but are not limited to, methoxy, ethoxy, propoxy, isopropoxy.

The term "5- to 8-membered nitrogen-containing saturated heterocycle" includes 5- to 8-membered nitrogen-containing saturated heterocycle containing 1 to 3 hetero atoms selected from 2 or 3 nitrogen atoms, 0 or 1 oxygen atom and 0 or 1 sulfur atom wherein at least two nitrogen atoms are contained in the ring. Specific examples include pyrrolidine, piperidine, perhydroazepine, imidazolidine, piperazine, morpholine, thiomorpholine, perhydro-1,4-diazepine, and the like.

Examples of the substituent group for the nitrogen-containing saturated heterocycle include preferably methyl group, ethyl group, propyl group, hydroxymethyl group, hydroxyethyl group, carbonyl group, hydroxy group and halogen atom, and more preferably hydroxy group and halogen atom. The nitrogen-containing saturated heterocycle may be substituted with the same or different 1 to 4 said substituent groups.

More preferable examples of the conjugated compounds in which a low molecular weight compound(s) having a pyrimidine skeleton(s) and a lipid(s) derived from squalene or squalane are chemically linked via a spacer(s) include:

(4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide (Patent Document 12, compound of Example 1, Formula (2) as below);

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one (Patent Document 12, compound of Example 2);

(4E,8E,12E,16E,20E)-1-(4-{4-[(2-amino-4-{[(2S)-1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one (Patent Document 12, compound of Example 3);

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide (Patent Document 12, compound of Example 4, Formula (3) as below);

4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide (Patent Document 12, compound of Example 5); and pharmaceutically acceptable salts thereof.

More preferred examples of the conjugated compounds in which a low molecular weight compound(s) having a pyrimidine skeleton(s) and a lipid(s) derived from squalene or squalane are chemically linked via a spacer(s) include (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide (Patent Document 12, compound of Example 1, Formula (2) as below), 4-[(2-amino-4-{[(2S)-1-hydroxypentan-2-yl]amino}-6-methylpyrimidin-5-yl)methyl]-N-(2-{[(4E,8E,12E,16E, 20E)-4,8,12,17,21,25-hexamethylhexacosa-4,8,12,16,20,24-hexaenoyl]amino}ethyl)-3-methoxybenzamide (Patent Document 12, compound of Example 4, Formula (3) as below), and
pharmaceutically acceptable salts thereof.

of hemagglutinin, to which an antibody induced by a conventional influenza HA split vaccine binds, is mutated.

In a preferred embodiment, the influenza HA split vaccine of the present invention binds to a LAH binding monoclonal antibody more strongly than a current HA split vaccine. For (2)

(3)

Examples of pharmaceutically acceptable salts as used herein include acid addition salts or base addition salts. Examples of the acid addition salt include acid addition salts with inorganic or organic acids such as hydrochloric acid, hydrobromic acid, sulfuric acid, trifluoroacetic acid, citric acid and maleic acid. Examples of the base addition salt include alkali metal salts such as sodium salt and potassium salt, alkaline earth metal salts such as calcium salt, and ammonium salt.

As used herein, a universal influenza vaccine antigen refers to an influenza vaccine antigen that induces an antibody which may broadly protect influenza including variant viruses (for example, a cross-protective antibody).

The universal influenza vaccine antigen includes, for example, particle antigens comprising an influenza virus-derived protein(s) disclosed in Patent Document 14 and influenza HA antigens disclosed in Non Patent Documents 6, 7 and 8.

Preferred example of the universal influenza vaccine antigen includes "an influenza HA split vaccine antigen which produces an antibody that binds to a LAH of a HA stem region". More preferably, "an influenza HA split vaccine antigen, wherein the HA stem region is exposed outside, capable of producing an antibody that binds to a LAH of a HA stem region" (hereinafter referred to as the influenza HA split vaccine of the present invention) is exemplified, which may be manufactured, for example, by a method comprising a step of applying an acidic treatment described below.

Since the influenza HA split vaccine of the present invention induces an antibody that binds to LAH in the stem region of hemagglutinin which is less likely to cause antigenic variation, the influenza HA split vaccine of the present invention may be effective against an influenza virus in which an antigenic site, which is located in the head region example, the influenza HA split vaccine binds to the LAH binding monoclonal antibody at least 1.05 times, preferably at least 1.1 times, more preferably at least 1.5 times, and even more preferably at least two times more strongly than the current HA split vaccine. In this context, "the influenza HA split vaccine binds at least 1.05 times, at least 1.1 times, at least 1.5 times, or at least two times more strongly than the current HA split vaccine" means, for example, that the reciprocal of the antibody concentration at the time when an absorbance determined by regression is 0.7 is at least 1.05 times, at least 1.1 times, at least 1.5 times, or at least two times the reciprocal of the antibody concentration of the current HA split vaccine. In a preferred embodiment, the binding capacity of the influenza HA split vaccine of the present invention to the LAH binding monoclonal antibody is higher than that of the current HA split vaccine. Although the upper limit is not particularly limited, the binding capacity may be in a range of, for example, 1.05 to 200 times, 1.1 to 150 times, 1.5 to 100 times, or 2 to 50 times. Alternatively, the range of the binding capacity of the influenza HA split vaccine of the present invention to the LAH binding monoclonal antibody compared to that of the current HA split vaccine may be indicated by a combination of the lower limit value selected from 1.05, 1.1, 1.5, 2, 3, 4, and 5 and the upper limit value selected from 200, 150, 100, 50, 30, and 20. For the measurement of the binding capacity of the influenza HA split vaccine to the LAH binding monoclonal antibody, any method can be used without particular limitations, and a common method known to those skilled in the art can be employed. For example, the binding capacity can be measured by a method described in examples of the present application.

In the present application, the "LAH binding monoclonal antibody" means a monoclonal antibody which binds to the LAH. For the production of the monoclonal antibody, any method may be used without particular limitations, and a common method known to those skilled in the art may be employed. In the measurement of the binding capacity of the influenza HA split vaccine to the LAH binding monoclonal antibody, it is assumed that the LAH binding monoclonal antibody is capable of binding to a peptide corresponding to at least a portion of the LAH of an influenza virus from which the influenza HA split vaccine is derived.

In this application, the "current HA split vaccine" means a vaccine from which lipid components that become pyrogens are removed through a treatment of the whole-virus vaccine with ether, and can be produced by a method described in Example 1 of the present application, for example. The current HA split vaccine may also be an influenza HA split vaccine produced without being subjected to an acidic treatment, in contrast with the influenza HA split vaccine of the present invention prepared by a method including the following acidic treatment.

An example of the method for producing the influenza HA split vaccine of the present invention is described below. The method for producing an influenza HA split vaccine includes a step of subjecting an influenza HA split vaccine to an acidic treatment.

An influenza HA split vaccine is prepared through a treatment of a whole-virus vaccine with ether to remove lipid components which become pyrogens. The influenza HA split vaccine has HA protein as the main ingredient because the influenza HA split vaccine is produced by collecting the HA protein, which is required for immunization, from the surfaces of the virus particles by density gradient centrifugation.

Glycoprotein called "spike protein" protrudes from the surface of an influenza virus (FIG. 1). An influenza A virus has two types of spike proteins, namely, HA and NA (neuraminidase), which help the virus cause the infection. HA binds to a cell to be infected and helps the entry of the virus into the cell. HA frequently causes antigenic variation. NA unbinds the infected cell from HA, and serves to release the replicated viruses from the cell.

An acidic treatment on the influenza HA split vaccine changes the structure of the HA protein to a structure called membrane fusion-type. In the membrane fusion-type HA protein, the stem region is exposed outside from the viral membrane instead of the head region, with a large structural change in the conformation of an antigen stem. The present inventors have found in vivo that when the membrane fusion-type HA protein is used as a vaccine, an antibody that binds to a LAH of the stem region is induced, and that this antibody has a protective effect against a virus strain that causes antigenic variation.

The acidic treatment is not particularly limited, and may be performed at a pH of, for example, 3.0 to 6.5, preferably 4.0 to 6.0, and more preferably 4.4 to 5.8. The acid for use in the acidic treatment is not particularly limited, and may be, for example, phosphoric acid, citric acid, maleic acid, or any other suitable acid.

The production of the influenza HA split vaccine of the present invention may include performing a formalin treatment. In a preferred embodiment, the acidic treatment of the influenza HA split vaccine is performed before the formalin treatment. In preparing an influenza HA split vaccine antigen of the present invention (an influenza HA split vaccine antigen capable of producing an antibody that binds to the LAH of the HA stem region), a HA fraction for use for the current influenza HA split vaccine is subjected to an acidic treatment, and then to a formalin treatment. This makes it possible to obtain an influenza HA split vaccine antigen which produces a cross-reactive antibody more effectively, and thus, is more preferable as a universal influenza vaccine antigen. That is, in a preferred embodiment of the present application, a HA fraction from which fat solvents are removed through a treatment of the virus particles with ether or any other appropriate agents is subjected to an acidic treatment, and then to a formalin treatment.

In a preferred embodiment of the present application, the influenza HA split vaccine before the acidic treatment is a split vaccine which has not undergone the formalin treatment.

Commercially available Influenza HA Vaccine (trade name) has already undergone a treatment with formaldehyde or a substance having an equivalent action after the virus is decomposed by ether or any other appropriate agents and fat solvents are removed, as described in Biological Products Standards (Mar. 30, 2004, Ministerial Notification No. 155 of Ministry of Health, Labor and Welfare, most recent revision on Nov. 30, 2018, Ministerial Notification No. 409). It is preferable not to use the commercially available Influenza HA Vaccine (trade name), which is one of the influenza HA split vaccines, for the production of the influenza HA split vaccine of the present invention because it has already been treated with formaldehyde or any other appropriate agents.

The concentration of formalin in a formalin treatment solution for used in the formalin treatment of the influenza HA split vaccine after the acidic treatment is, for example, 0.0005 v/v % to 10 v/v %, preferably 0.001 v/v % to 1 v/v %, more preferably 0.003 v/v % to 0.5 v/v %, and still more preferably 0.005 v/v % to 0.1 v/v %. It is preferable to use formalin of a medical grade.

Based on differences in antigenicity, HA of the influenza A virus is classified into 18 subtypes (H1 to H18), and NA into 9 subtypes (N1 to N9). The influenza HA split vaccine of the present invention is applicable to all of these subtypes. In addition, the method for producing the influenza HA split vaccine according to the present invention can produce a vaccine which is effective against not only the influenza A virus, but also an influenza B virus having HA. Thus, vaccines for the influenza A virus and the influenza B virus are within the scope of the influenza HA split vaccine of the present invention.

Preferred examples of the influenza HA split vaccines of the present invention include those derived from H3N2 influenza virus and H1N1 influenza virus.

In the present application, an "influenza HA split vaccine of a single HA subtype" refers to an influenza HA split vaccine of a single HA subtype which is selected from the 18 subtypes (H1 to H18) of the influenza A virus, or the influenza B virus. As long as with the single HA subtype, the NA subtypes may be identical or different. Preferred HA subtypes include H1, H3, and B.

To produce a mixed vaccine containing two or more HA subtypes, influenza HA split vaccines each of which is of a single HA subtype are subjected to an acidic treatment, and a plurality of (two or more) influenza HA split vaccines thus obtained can be mixed together. Alternatively, a mixed vaccine can also be produced by performing an acidic treatment on an influenza HA split vaccine previously prepared by mixing vaccines of two or more HA subtypes. To inoculate the vaccine as a vaccine including two or more subtypes, the vaccine preferably includes one to three subtypes selected from the group consisting of H1, H3, and B.

The influenza HA split vaccine according to the present invention produces an antibody that binds to a LAH which is less likely to cause variation. Therefore, the vaccine can be cross-protective against an influenza virus, which is known as an antigenic variant, as long as the virus has the same HA subtype. Furthermore, the influenza HA split vaccine obtained by the production method according to the present invention may be cross-reactive between HA subtypes of similar amino acid sequences of LAH (e.g., H3 and H7).

The influenza HA split vaccine obtained by the above production method has a protective effect against a virus strain that causes antigenic variation. For example, if a current HA split vaccine is prepared from particles of H3N2 influenza virus (A/Fujian/411/02(H3N2)) and subjected to an acidic treatment, the vaccine may have a protective effect against infection of not only A/Fujian/411/02(H3N2), but also A/Guizhou/54/89(H3N2), A/OMS/5389/88(H3N2), A/Beijing/32/92(H3N2), A/England/427/88(H3N2), A/Johannesburg/33/94(H3N2), A/Leningrad/360/86(H3N2), A/Mississippi/1/85(H3N2), A/Philippines/2/82(H3N2), A/Shangdong/9/93(H3N2), A/Shanghai/16/89(H3N2), A/Shanghai/24/90(H3N2), A/Sichuan/2/87(H3N2), A/Kitakyushyu/159/93(H3N2), A/Akita/1/94(H3N2), A/Panama/2007/99(H3N2), A/Wyoming/03/03(H3N2), A/New York/55/2004(H3N2) or A/Hiroshima/52/2005(H3N2), for example. Also, for example, if a current HA split vaccine is prepared from particles of H1N1 influenza virus (A/Puerto Rico/8/34(H1N1)) and subjected to an acid treatment, the vaccine may also have a protective effect against infection of not only A/Puerto Rico/8/34(H1N1), but also A/Narita/1/09 (H1N1), A/Beijing/262/95(H1N1), A/Brazil/11/78 (H1N1), A/Chile/1/83(H1N1), A/New Jersey/8/76(H1N1), A/Taiwan/1/86(H1N1), A/Yamagata/32/89(H1N1), A/New Caledonia/20/99(H1N1), A/Solomon Islands/3/2006(H1N1), A/Brisbane/59/2007(H1N1) or A/Mexico/4108/2009 (H1N1), for example.

The influenza HA split vaccine of the present invention has an enhanced ability to induce anti-stem IgG2 antibodies by combining a compound that enhances the physiological activity of TLR7, and exhibits excellent vaccine activity.

One embodiment of the combination of a universal influenza vaccine antigen and a vaccine adjuvant herein includes a combination of a universal influenza vaccine antigen(s) selected from particle antigens comprising an influenza virus-derived protein disclosed in Patent Document 14, influenza HA antigens disclosed in Non Patent Documents 6, 7 and 8, and membrane fusion-type influenza HA split vaccine antigens; and a vaccine adjuvant(s) selected from alum, emulsions (for example, Freund's adjuvant, MF59$^{(Registered\ trademark)}$, AddaVax™, AS03, etc.), substances that enhance the physiological activity of NOD receptors, substances that enhance the physiological activity of RIG-I receptors, substances that enhance the physiological activity of C-type lectin receptors, substances that enhance the physiological activity of cytosolic DNA receptors, substances that enhance the physiological activity of STING, and substances that enhance the physiological activity of TLR.

Another embodiment of the combination of a universal influenza vaccine antigen and a vaccine adjuvant includes a combination of an influenza HA split vaccine antigen(s) which produces an antibody that binds to a LAH of a HA stem region; and a substance(s) which enhances the physiological activity of TLR.

Another embodiment of the combination of a universal influenza vaccine antigen and a vaccine adjuvant includes a combination of an influenza HA split vaccine antigen(s), wherein the HA stem region is exposed outside, capable of producing an antibody that binds to a LAH of a HA stem region; and a substance(s) which enhances the physiological activity of TLR7 selected from low molecular weight compounds which enhance the physiological activity of TLR7, and conjugated compounds in which a low molecular weight compound(s) which enhances the physiological activity of TLR7 and a lipid(s) are chemically linked via a spacer(s).

Another embodiment of the combination of a universal influenza vaccine antigen and a vaccine adjuvant includes a combination of an influenza HA split vaccine antigen(s), wherein the HA stem region is exposed outside, capable of producing an antibody that binds to a LAH of a HA stem region; and a conjugated compound(s) in which a low molecular weight compound(s) which enhances the physiological activity of TLR7 and a lipid(s) are chemically linked via a spacer(s), has a molecular weight of 200 to 600, and has an adenine skeleton(s), a pyrimidine skeleton(s), an imidazoquinoline skeleton(s), an imidazopyridine skeleton(s), or a quinazoline skeleton(s).

Another embodiment of the combination of a universal influenza vaccine antigen and a vaccine adjuvant includes a combination of an influenza HA split vaccine antigen(s) wherein the HA stem region, which is exposed outside, enhances the antigenicity of the LAH of the HA stem region, capable of producing an antibody that binds to the LAH of the HA stem region; and a conjugated compound(s) in which a low molecular weight compound(s) having a pyrimidine skeleton(s) and a lipid(s) derived from squalene or squalane are chemically linked via a spacer(s).

Another embodiment of the combination of a universal influenza vaccine antigen and a vaccine adjuvant includes a combination of an influenza HA split vaccine antigen(s) wherein the HA stem region, which is exposed outside, enhances the antigenicity of the LAH of the HA stem region, capable of producing an antibody that binds to the LAH of the HA stem region; and a compound(s) that enhances the physiological activity of TLR7 represented by Formula (1) or a pharmaceutically acceptable salt(s) thereof;

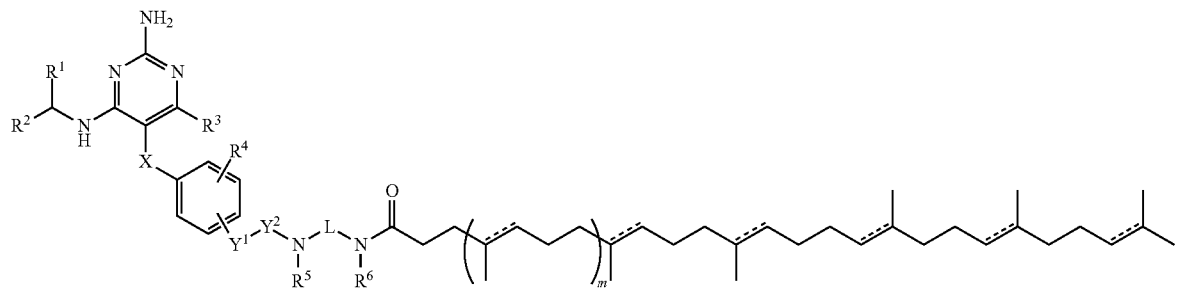

(1)

wherein
X represents methylene,
R¹ represents a hydrogen atom or an alkyl group having 1 to 3 carbon atoms which may be substituted with hydroxy group,
R² represents a hydrogen atom or an alkyl group having 1 to 6 carbon atoms,
R³ represents an alkyl group having 1 to 3 carbon atoms,
R⁴ represents a hydrogen atom, a halogen atom, a hydroxy group, an alkyl group having 1 to 3 carbon atoms, or an alkoxy group having 1 to 3 carbon atoms,
Y¹ represents a single bond or methylene,
Y² represents a single bond or —C(O)—,
L represents a straight chain alkylene having 2 or 3 carbon atoms,
R⁵ and R⁶ independently represent a hydrogen atom or an alkyl group having 1 to 3 carbon atoms, or R⁵ and R⁶ are taken together to form a substituted or unsubstituted 5- to 8-membered nitrogen-containing saturated heterocycle, provided that when the 5- to 8-membered nitrogen-containing saturated heterocycle is substituted, it is substituted with the same or different 1 to 4 substituents selected from hydroxy group and halogen atom,
m represents 0 or 1,
====== are all double bonds.

Another embodiment of the combination of a universal influenza vaccine antigen and a vaccine adjuvant includes a combination of an influenza HA split vaccine antigen(s) wherein the HA stem region, which is exposed outside, enhances the antigenicity of the LAH of the HA stem region, capable of producing an antibody that binds to the LAH of the HA stem region; and a compound(s) that enhances the physiological activity of TLR7 selected from the following compounds:
(4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;
(4E,8E,12E,16E,20E)-1-(4-{4-[(2-amino-4-{[(2S)-1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one;
(4E,8E,12E,16E,20E)-1-(4-{4-[(2-amino-4-{[(2S)-1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one;
4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide;
4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide; and
a pharmaceutically acceptable salt thereof.

Another embodiment of the combination of a universal influenza vaccine antigen and a vaccine adjuvant includes a combination of an influenza HA split vaccine antigen(s) wherein the HA stem region, which is exposed outside, enhances the antigenicity of the LAH of the HA stem region, capable of producing an antibody that binds to the LAH of the HA stem region; and a compound(s) that enhances the physiological activity of TLR7 selected from the following compounds:
(4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;
4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; and
a pharmaceutically acceptable salt thereof.

Another embodiment of the combination of a universal influenza vaccine antigen and a vaccine adjuvant includes a combination of an influenza HA split vaccine antigen(s) capable of producing an antibody that binds to a LAH of a HA stem region, produced by subjecting an influenza HA split vaccine to an acidic treatment; and a compound(s) that enhances the physiological activity of TLR7 selected from the following compounds:
(4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;
4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; and
a pharmaceutically acceptable salt thereof.

As used herein, the term "a prophylactically effective amount" is the amount of universal influenza vaccine antigen and/or vaccine adjuvant required to confer a benefit in influenza prevention.

In the present application, the universal influenza vaccine antigen and the vaccine adjuvant may be contained together in one composition and may be formulated in separate compositions, but from the perspective of reducing patient burden, it is preferred that the universal influenza vaccine antigen and the vaccine adjuvant be contained in one composition so that they can be administered simultaneously when administered.

When the universal influenza vaccine antigen and the vaccine adjuvant are formulated in separate compositions, the administration routes of the universal influenza vaccine antigen composition and the vaccine adjuvant composition may be the same or different. In the present application, the vaccine antigen and the vaccine adjuvant may be administered simultaneously or by time difference, i.e., the vaccine antigen composition and the vaccine adjuvant composition may be administered simultaneously or separately (for example, the vaccine adjuvant composition is administered before or after administration of the vaccine antigen composition). The universal influenza vaccine antigen composition and the vaccine adjuvant composition may be provided as a kit comprising them.

As used herein, the compositions comprising a universal influenza vaccine antigen and/or a vaccine adjuvant may be prepared by a usual method, with the addition of one or more pharmaceutically acceptable diluents or carriers, for example, in the form of oral agents such as tablets, capsules, granules, powders, troche, syrups, emulsions, suspensions, and the like, or parenteral agents such as external agents, suppositories, injections, eye drops, intranasal agents, pulmonary agents, and the like. Preferred examples of the formulations include injectable or intranasal solutions, or lyophilized formulations prepared by lyophilizing said solutions.

Examples of the injectable solutions include emulsions and liposomes comprising an aqueous solution and oleaginous compositions, aqueous solution formulations or aqueous suspension formulations in which the universal influenza vaccine antigen and/or the vaccine adjuvant (for example, compounds represented by formula (1) or pharmaceutically acceptable salts thereof) are dissolved or dispersed in water, or oleaginous solution formulations or oleaginous suspension formulations in which the universal influenza vaccine antigen and/or the vaccine adjuvant (for example, compounds represented by formula (1) or pharmaceutically acceptable salts thereof) are dissolved or dispersed in oil.

Examples of the aqueous solutions, the aqueous solution formulations or the aqueous suspension formulations include aqueous solutions or aqueous suspensions etc. comprising distilled water for injection and optionally comprising buffers, pH adjusters, stabilizers, isotonizers and/or emulsifiers.

Examples of the oleaginous compositions, the oleaginous solution formulations or the oleaginous suspension formulations include compositions containing vegetable oils and fats, animal oils and fats, hydrocarbons, fatty acid esters, phospholipids, etc., and more specifically, a composition containing squalene, squalane, etc.

Examples of the emulsifiers include hydrophilic surfactants and hydrophobic surfactants.

The composition herein may comprise one or more pharmaceutically acceptable carriers selected from the group consisting of sucrose, sucralose, trehalose, mannitol, glycine, methionine, citric acid, lactic acid, tartaric acid, acetic acid, trifluoroacetic acid and a pH adjuster.

The method of administration of the composition, kit, or the like in the present application can be appropriately selected according to conditions such as the type of disease, the condition of the subject, and the target site. Examples of the method of administration include parenteral administration, specifically, intravascular (for example, intravenous), subcutaneous, intradermal, intramuscular, transnasal, and transdermal administration.

In the present application, the doses of the vaccine adjuvant and the vaccine antigen are not particularly limited, and are appropriately selected according to the method of administration, the subject, the age of the subject, the dosage form, the route of administration, etc.

For example, when the vaccine adjuvant is a compound of formula (1) or a pharmaceutically acceptable salt thereof, the compound of formula (1) or a pharmaceutically acceptable salt thereof may be administered to a warm-blooded animal in a unit dose ranging from usually 5 to 5000 mg/m$^2$ of body surface area, i.e., about 0.1 ng/kg to 100 mg/kg, which usually provides a prophylactically effective dose. Unit dosage forms such as injections, tablets or capsules usually contain, for example, 1 ng to 250 mg of a compound of formula (1) or a pharmaceutically acceptable salt thereof, and preferably, used at a dose ranging from 1 ng to 50 mg/kg per day. However, the daily dose may vary depending on the host to be treated, the route of administration and the severity of the disease being treated. Thus, the optimal dose can be determined by a practitioner who treats individual patient or warm-blooded animal. If the vaccine adjuvant is administered concurrently with the universal influenza vaccine antigen, the vaccine adjuvant is administered, for example, according to the following schedule of administration of the universal influenza vaccine antigen. Even when the vaccine adjuvant is administered separately from the universal influenza vaccine antigen, it may be administered, for example, in consideration of the following administration schedule of the universal influenza vaccine antigen.

In the present application, the dosage of the universal influenza vaccine antigen (for example, influenza HA split vaccines of the present invention), the dosage form of the composition, the number of doses, the time required for a single administration, and the like can be appropriately selected depending on the conditions such as the age of the subject and the target site. The universal influenza vaccine antigens (for example, influenza HA split vaccines of the present invention) may be administered in a single dose only or may be administered in an initial dose and a booster dose which is administered after a predetermined period of time following the initial dose, for example. The period from the initial vaccination to the booster vaccination is not particularly limited, but is, for example, 20 days to 3 years, preferably 3 months to 2 years, and more preferably 6 months to 1 year. The amounts of a universal influenza vaccine antigen for a primary vaccination and a booster vaccination are not particularly limited, but is, for example, 1 μg to 200 μg per dose, preferably 10 μg to 30 μg per dose, and more preferably 15 μg per dose. For example, one dose is 0.5 mL. The amounts of a substance that enhances the physiological activity of TLR7 in a primary vaccination and a booster vaccination are usually 0.0001 mg to 1000 mg, preferably 0.001 mg to 1000 mg, and more preferably 0.1 mg to 10 mg. For a primary vaccination and a booster vaccination, the method of administration is not particularly limited, but may be, for example, nasal, subcutaneous, intradermal, transdermal, intraocular, mucosal, or oral administration, preferably intramuscular administration.

As used herein, "warm-blooded animal" includes human and non-human animals. Non-human animals include, but are not limited to, for example, mammals such as non-human primates, sheep, dogs, cats, horses, and cattle. Among warm-blooded animals, human, especially human requiring the prevention of influenza, is preferable.

One embodiment of the method for preventing influenza herein includes a method comprising administering a composition comprising the universal influenza vaccine antigen(s) and a vaccine adjuvant(s) described mentioned above. Another embodiment includes a method comprising administering a universal influenza vaccine antigen composition and a vaccine adjuvant composition.

EXAMPLE

Hereinafter, the present invention will be described in detail by Examples, but the present invention is not limited thereto.

Example 1: Influenza HA Split Vaccine of the Present Invention

1. Preparation of HA Split Vaccine

Tween 80 was added to particles of H3N2 influenza virus (strain X31) or particles of H1N1 influenza virus (A/Puerto Rico/8/34 strain) suspended in phosphate buffered saline to a final concentration of 0.1 v/v %, and suspended therein. Diethyl ether was added and suspended, and the suspension was left stand until an aqueous layer and a diethyl ether layer were completely separated, and then the diethyl ether layer was removed. After repeating this ether extraction, diethyl ether remaining in the recovered aqueous layer was distilled off at normal pressure to obtain an HA split vaccine.

2. Acidic Treatment

The HA split vaccine was suspended in phosphate buffered saline, and an acidic treatment was then performed by adding 0.15 M citrate buffer (pH 3.5) to bring the pH to 5.0. After standing at room temperature for 30 minutes, 1 M Tris buffer (pH 8.0) was added so that the pH was returned to 7.3. Thereafter, centrifugation was performed to obtain a membrane fusion-type HA split vaccine. Formalin was added to the membrane fusion-type HA split vaccine thus prepared to a final concentration of 0.05 v/v %, and left stand for several days.

A current HA split vaccine was prepared in the same manner as described in 1 above except that no acidic treatment was provided.

3. Measurement of Titer of Anti-LAH Antibody by ELISA 3-1. Inoculation of H3N2 Influenza Vaccine BALB/c mice (female, 6 to 12 weeks old) were intraperitoneally inoculated with the current H3N2 HA split vaccine or the membrane fusion-type HA split vaccine (10 µg of vaccine+10 v/v % of AddaVax adjuvant (InvivoGen) dissolved in phosphate buffered saline to a liquid volume of 200 µl). Twenty eight days after the initial inoculation, the mice were intraperitoneally inoculated with the membrane fusion-type HA vaccine (10 µg of the vaccine alone was dissolved in phosphate buffered saline to a liquid volume of 200 µl). At least 14 days after the additional inoculation, blood was collected from the mice inoculated with the vaccine, from which sera were collected.

3-2. Measurement by ELISA

The concentration of the anti-LAH antibody in the sera of BALB/c mice intraperitoneally inoculated with the current H3N2 HA split vaccine or the membrane fusion-type HA split vaccine was measured by ELISA (Enzyme-Linked Immuno Sorbent Assay) in the following manner.

Specifically, a synthetic peptide (H3; Ac-RIQDLEKYVEDTKIDLWSYNAELLVA-LENQHTIDLTDSEMNKLFEKTRRQLRENADYKD DDDKC) (SEQ ID NO: 1) corresponding to a portion (long alpha helix) of the stem portion was dissolved in phosphate buffered saline (pH 7.3) at 10 µg/ml, and added to 96-well plates by 100 µl each. After standing overnight at 4° C., each well was washed three times with phosphate buffered saline, and 150 µl of phosphate buffered saline containing 1 v/v % bovine serum albumin was added. After standing at room temperature for two hours, each well was washed three times with phosphate buffered saline. Then, 100 µl of a mouse serum serially diluted with phosphate buffer containing 0.05 v/v % of Tween 20 and 1 v/v % bovine serum albumin, and 100 µl of a standard monoclonal antibody of known concentration (H3; clone name V15-5) were added to each well. After standing at room temperature for two hours, each well was washed three times with phosphate buffered saline (containing 0.05 v/v % of Tween 20), and 100 µl of a peroxidase-labeled anti-mouse IgG antibody (Southern Biotech) diluted with phosphate buffered saline containing 0.05 v/v % Tween 20 and 1 v/v % bovine serum albumin was added to each well. After standing at room temperature for two hours, each well was washed three times with phosphate buffered saline (containing 0.05 v/v % of Tween 20). Then, 30 mg of o-phenylendiamine tablet (Sigma) and 24 µl of 30% hydrogen peroxide solution (30% w/w; Sigma) were added to 60 ml of citrate buffer (pH 5.0) as a substrate, and 100 µl of the resultant was added to each well. After the color development, 50 µl of 1 mol/L sulfuric acid (Wako Pure Chemical Industries, Ltd.) was added to stop the reaction, and an absorbance value at 490 nm was measured using a Microplate Reader 450 (Biorad).

Figure 2:
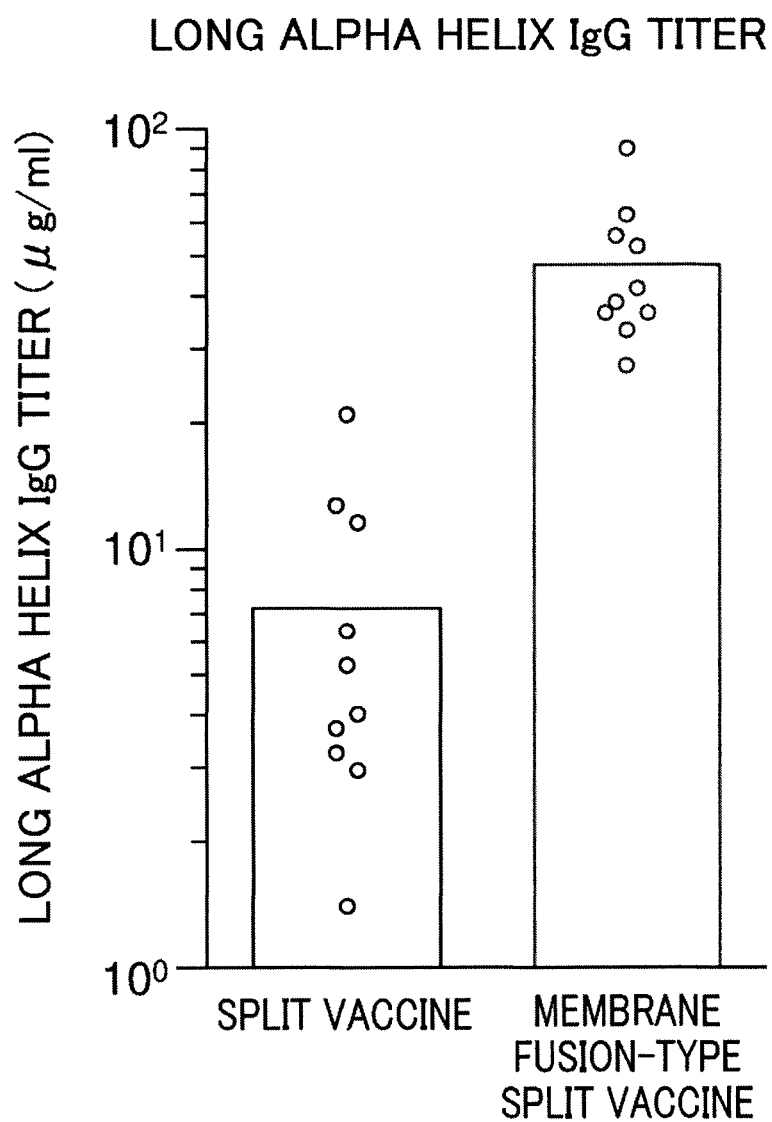

As shown in FIG. 2, the titer of the anti-LAH antibody in the serum of the BALB/c mice intraperitoneally inoculated with the membrane fusion-type HA split vaccine was significantly higher than the titer of the anti-LAH antibody in the serum of BALB/c mice intraperitoneally inoculated with the current HA split vaccine.

4. Cross-Protection Against Antigenic Variant

In an experiment on protection against infection with the H3N2 virus, 200 µl of a serum collected from uninoculated mice, 200 µl of a serum collected from mice inoculated with the current H3N2 HA split vaccine, or 200 µl of a serum collected from mice inoculated with the membrane fusion-type HA split vaccine was intraperitoneally administered to BALB/c mice (female, 6 to 12 weeks old).

Three hours after the serum administration, another H3N2 influenza virus (A/Guizhou/54/89) having different antigenicity from the vaccine strain was intranasally administered at 5 mouse lethal dose 50 (five times the amount of virus lethal to 50% of mice) under anesthesia.

Mice were weighed and observed daily for 21 days from the viral infection to study the change in body weight and the survival rate. The humane endpoint was set at 25% body weight loss.

Figure 3:
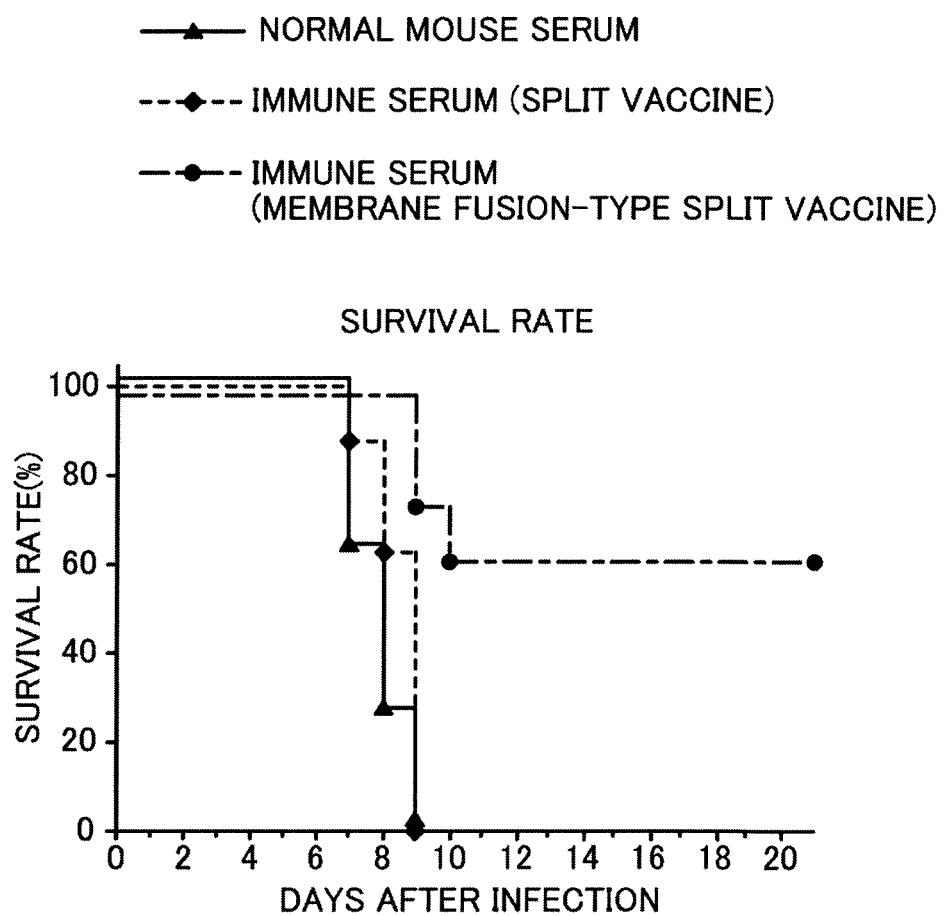

As shown in FIG. 3, regarding the BALE/c mice inoculated with the membrane fusion-type HA split vaccine, the decrease in the survival rate was significantly curbed on and after the ninth day after the infection with the other H3N2 influenza virus of different antigenicity.

5. Measurement of Titer of Anti-LAH Antibody by ELISA

5-1. Particles of H1N1 Influenza Virus

C57BL/6 mice (female, 6 to 12 weeks old) were intraperitoneally inoculated with a current H1N1 HA split vaccine or a membrane fusion-type HA split vaccine (10 µg of vaccine+10 µg of CpG-ODN 1760 suspended in phosphate buffered saline and mixed with an equal volume of Freund's incomplete adjuvant (ROCKLAND) to a liquid volume of 200 µl). Twenty eight days after the initial inoculation, the mice were intraperitoneally inoculated with the membrane fusion-type HA split vaccine (10 µg of vaccine+10 µg of CpG-ODN suspended in phosphate buffered saline and mixed with an equal volume of Freund's incomplete adjuvant (ROCKLAND) to a liquid volume of 200 µl, in the same manner as the initial inoculation). At least 14 days after the additional inoculation, blood was collected from the mice inoculated with the vaccine, from which sera were collected.

5-2. Measurement by ELISA

The concentration of the anti-LAH antibody in the sera of C57BL/6 mice intraperitoneally inoculated with the current H1N1 HA split vaccine or the membrane fusion-type HA split vaccine was measured by ELISA in the following manner.

The measurement was performed in the same manner as described above except that a synthetic peptide (H1; Ac-RIENLNKKVDDGFLDIWTYNAELLVLLEN-ERTLDYHDSNVKNLYEKVRSQLKNNADYKD DDDKC) (SEQ ID NO: 2) corresponding to a portion (long alpha helix) of the stem portion was used and a standard monoclonal antibody of known concentration (H1; clone name F2) was used.

Figure 4:
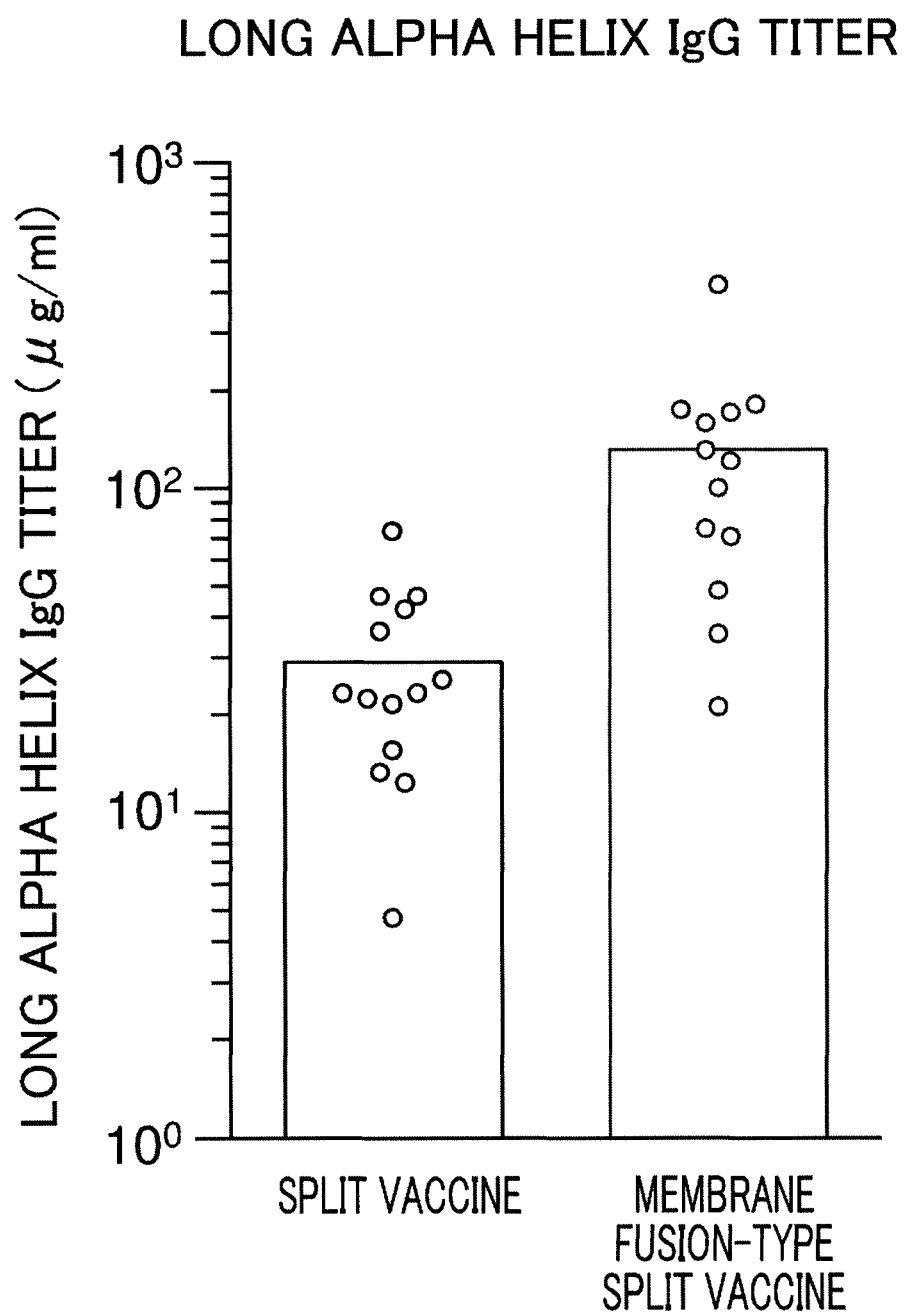
Figure 5:
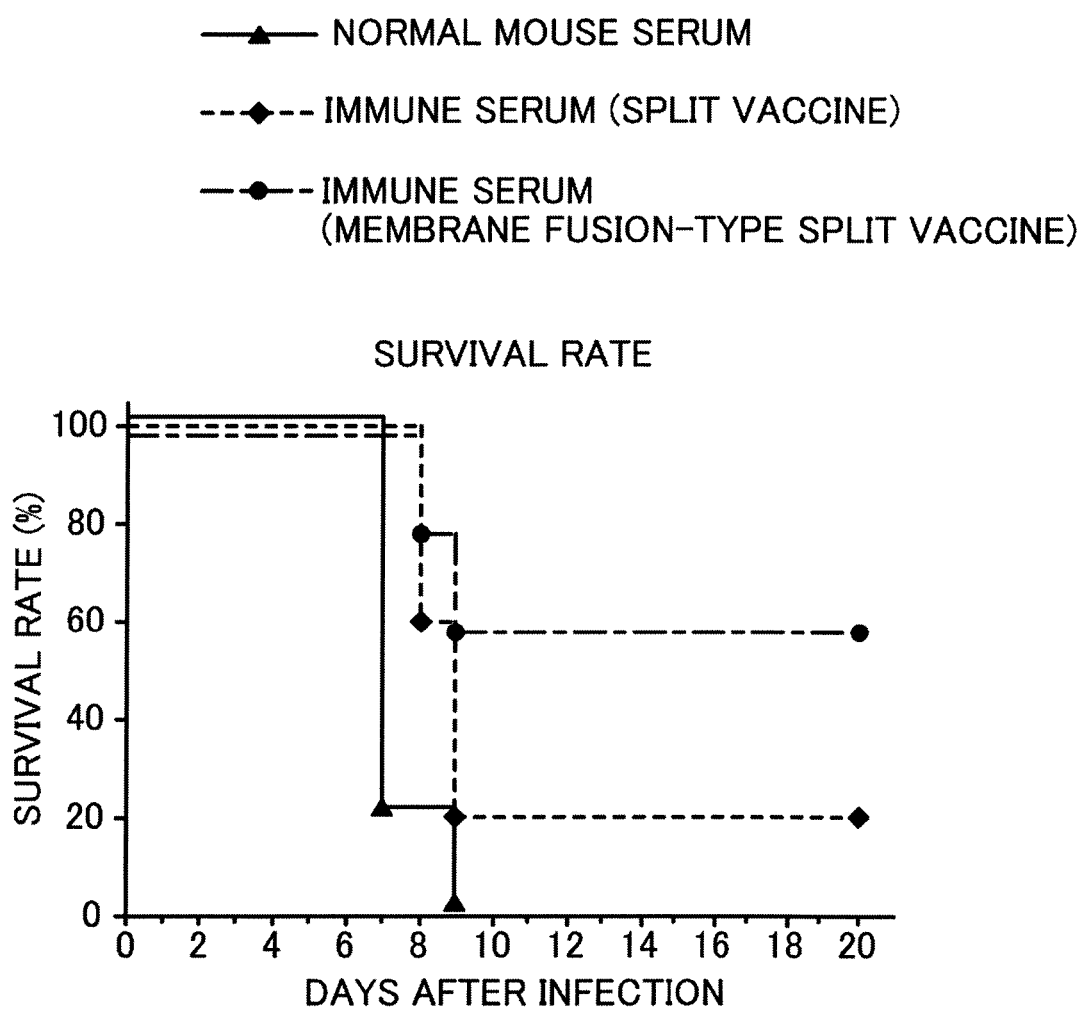

As shown in FIG. 4, the titer of the anti-LAH antibody in the sera of the C57BL/6 mice intraperitoneally inoculated with the membrane fusion-type HA split vaccine was significantly higher than the titer of the anti-LAH antibody in the sera of the C57BL/6 mice intraperitoneally inoculated with the current HA split vaccine.

6. Cross-Protection Against Antigenic Variant

In an experiment on protection against infection with the H1N1 virus, 200 µl of a serum collected from uninoculated mice, 200 µl of a serum collected from mice inoculated with the current H1N1 HA split vaccine, or 200 µl of a serum collected from mice inoculated with the membrane fusion-type HA split vaccine was intraperitoneally administered to C57BL/6 mice (female, 6 to 12 weeks old).

Three hours after the serum administration, another H1N1 influenza virus (A/Narita/1/09) having different antigenicity from the vaccine strain was intranasally administered at 5 mouse lethal dose 50 (five times the amount of virus lethal to 50% of mice) under anesthesia.

Mice were observed daily for 20 days from the viral infection to study the survival rate. As shown in FIG. 5, regarding the C57BL/6 mice inoculated with the membrane fusion-type HA split vaccine, the decrease in the survival rate was significantly curbed on and after the ninth day after the infection with the other H1N1 influenza virus of different antigenicity.

7. Binding Capacity of Antibody to LAH Epitope

Binding of anti-LAH monoclonal antibodies (#1 to #5 in FIG. 6) prepared from murine or human peripheral blood infected with strain X31 to a current HA split vaccine or a membrane fusion-type HA split vaccine was measured by ELISA (Enzyme-Linked Immuno Sorbent Assay). The current HA split vaccine or membrane fusion-type HA split vaccine of an H3N2 influenza virus (strain X31) was dissolved in phosphate buffered saline (pH 7.3), and added to a 96-well plate by 50 μl each. After standing overnight at 4° C., each well was washed three times with phosphate buffered saline, and 150 μl of phosphate buffered saline containing 1 v/v % bovine serum albumin was added. After standing at room temperature for two hours, each well was washed three times with phosphate buffered saline (containing 0.05 v/v % of Tween 20), and 50 μl of the LAH binding monoclonal antibody serially diluted with phosphate buffer containing 1 v/v % bovine serum albumin was added. After standing overnight at 4° C., each well was washed three times with phosphate buffered saline (containing 0.05 v/v % of Tween 20), and 100 μl of a peroxidase-labeled anti-mouse IgG antibody (Southern Biotech) diluted with phosphate buffered saline containing 0.05 v/v % Tween 20 and 1 v/v % bovine serum albumin was added to each well. After standing at room temperature for two hours, each well was washed three times with phosphate buffered saline (containing 0.05 v/v % of Tween 20). Then, 30 mg of o-phenylendiamine tablet (Sigma) and 24 μl of 30% hydrogen peroxide solution (30% w/w; Sigma) were added to 60 ml of citrate buffer (pH 5.0) as a substrate, and 50 μl of the resultant was added to each well. After the color development, 25 μL of 1 mol/L sulfuric acid (Wako Pure Chemical Industries, Ltd.) was added to stop the reaction, and an absorbance value at 490 nm was measured using Microplate Reader 450 (Biorad). The change in binding capacity was calculated from the absorbance values measured with respect to the current HA split vaccine or the membrane fusion-type HA split vaccine.

As shown in FIG. 6, the binding capacity of the LAH binding monoclonal antibody to the membrane fusion-type HA split vaccine was 1.05 to 21 times greater than the binding capacity to the current HA split vaccine. The results show that an acidic treatment of the HA split vaccine enhances the binding capacity of the antibody to the LAH epitope.

Example 2: Composition Comprising TLR Agonist and Influenza HA Split Vaccine of The Present Invention 1. Preparation of Adjuvant Composition Containing Compound Which Enhances Physiological Activity of TLR7

Preparation Method of A-1

Two point nine six grams (2.96 g) of dimyristoylphosphatidylcholine (DMPC), 2.04 g of egg yolk phosphatidylglycerol (EPG), and 0.5 g of TLR7 agonist ((4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide) (hereinafter referred to as compound A) were each weighed, and 20 g of cyclohexane and 0.4 g of ethanol were added thereto so that they were dissolved in them. After filtration using a 0.2 μm membrane filter, and the filtrate was lyophilized. The resulting solid was dispersed in 9 v/v % sucrose aqueous solution. The mixture was subjected to an extruder to provide a liposome liquid. The liposome liquid passed through a 0.22 μm filter was lyophilized. Distilled water for injection was added to the resulting solid, at the time of use.

Preparation Method of A-2

Four milligrams (4 mg) of TLR7 agonist (methyl (4-{[[3-(6-amino-2-butoxy-8-oxo-7,8-dihydro-9H-purin-9-yl)propyl](3-piperidin-1-ylpropyl)amino]methyl}phenyl)acetate hydrochloride) (hereinafter referred to as compound B) was weighed, and suspended in 1 mL of 0.6 v/v % phosphate buffered saline containing 0.1 v/v % Tween 80 (pH 6).

Preparation Method of A-3

TLR7 agonist (Compound A) was dissolved in oily components (squalane, sorbitan trioleate, and α-tocopherol) so that the weight ratio of Compound A, squalane, sorbitan trioleate, α-tocopherol was 1:225:25:25. The aqueous components (sucrose, polysorbate 80 and sodium ascorbate) were dissolved in water for injection. The resulting mixture and the above oleaginous composition was mixed preliminarily. In this mixture, the weight ratio of Compound A, sodium ascorbate, polysorbate 80, sucrose was 1:10:25:500. The mixture was emulsified and dispersed, using an ultra-high-pressure emulsification disperser. After filtration through a 0.2 μm sterile filter, glass vials were filled with 1 mL of the mixture, followed by lyophilization. Distilled water for injection was added to the resulting solid, at the time of use.

2. Administration of the Composition of the Present Invention, Comprising an Influenza HA Split Vaccine and a Compound that Enhances the Physiological Activity of TLR7

The membrane fusion-type HA split vaccine derived from strain X31 (10 μg); and phosphate buffered saline; A-1 containing 50 μg of TLR7 agonist (Compound A); A-2 containing 200 μg of TLR7 agonist (Compound B); A-3 containing 10 μg of TLR7 agonist (Compound A); AddaVax adjuvant (InvivoGen) whose volume was equal to the liquid of membrane fusion-type HA split vaccine derived from strain X31; or a mixture of 10 μg of CpG-ODN1760 suspended in phosphate buffered saline and an equal volume of Freund's incomplete adjuvant (ROCKLAND); were mixed to give each composition. C57BL/6 mice (female, 6 to 12 week old) were inoculated intradermally in the thighs or intramuscularly in the thighs (50 μl into each thigh, 100 μl in total) with the above composition. After 3 weeks, the same mice were boosted with the same antigen and under the same conditions. Two weeks after the booster, blood was drawn, from which serum was collected.

3. Measurement by ELISA

The concentration of the anti-HA antibody in the sera of the mice was measured by ELISA in the following manner.

A recombinant HA protein (strain X31 or A/Uruguay/716/2007 of H3N2 influenza virus) was dissolved in phosphate buffered saline (pH 7.3) at 10 μg/ml, and added to 96-well plates by 100 μl each. After standing overnight at 4° C., each well was washed three times with phosphate buffered saline, and 150 μl of phosphate buffered saline containing 1 v/v % bovine serum albumin was added. After standing at room temperature for two hours, each well was washed three times with phosphate buffered saline. Then, 100 μl of a mouse serum serially diluted with phosphate buffer containing 0.05 v/v % Tween 20 and 1 v/v % bovine serum albumin, and 100 μl of a standard monoclonal antibody of known concentration (H3; clone name V15-5) were added to each well. After standing at room temperature for two hours, each well was washed three times with phosphate buffered saline (containing 0.05 v/v % Tween 20), and 100 μl of a peroxidase-labeled anti-mouse IgG1 antibody or IgG2c antibody (Southern Biotech) diluted with phosphate buffered saline containing 0.05 v/v % Tween 20 and 1 v/v % bovine serum albumin was added to each well. After standing at room temperature for two hours, each well was washed three times with phosphate buffered saline (containing 0.05 v/v % Tween 20). Then, 30 mg of o-phenylendiamine tablet (Sigma) and 24 μl of 30% hydrogen peroxide solution (30% w/w; Sigma) were added to 60 ml of citrate buffer (pH 5.0) as a substrate, and 100 μl of the resultant was added to each well. After the color development, 50 μl of 1 mol/L sulfuric acid (Wako Pure Chemical Industries, Ltd.) was added to stop the reaction, and an absorbance value at 490 nm was measured using a Microplate Reader 450 (Biorad).

Figure 7:
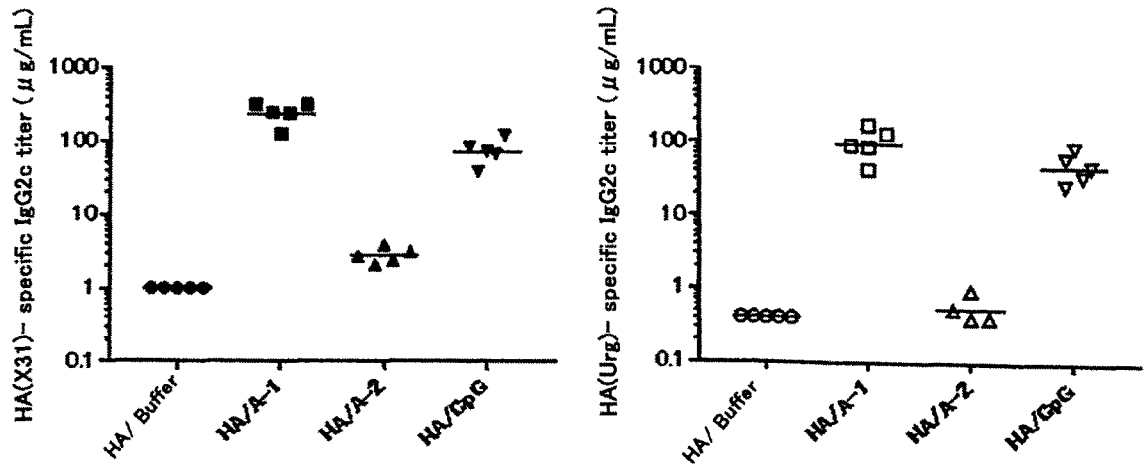

As shown in FIG. 7, the IgG2c titers against HA derived from strain X31 of all of the groups inoculated with the membrane fusion-type HA split vaccine with an adjuvant were significantly higher than that of the group inoculated with the membrane fusion-type HA split vaccine without adjuvant. The IgG2c titer against HA derived from strain X31 of A-1-administered group was higher than that of the group administered with CpG-ODN1760/Freund's incomplete adjuvant (CpG/IFA). Among the groups, A-1-administered group induced the highest IgG2c titer against HA derived from strain X31. Furthermore, for HA derived from Urg, similar results of the reactivity were observed. Thus, these results show the induction of cross-reactive IgG2 antibodies, which is highly effective in protection against infection, by the inoculation with the composition of the present application.

Figure 8:
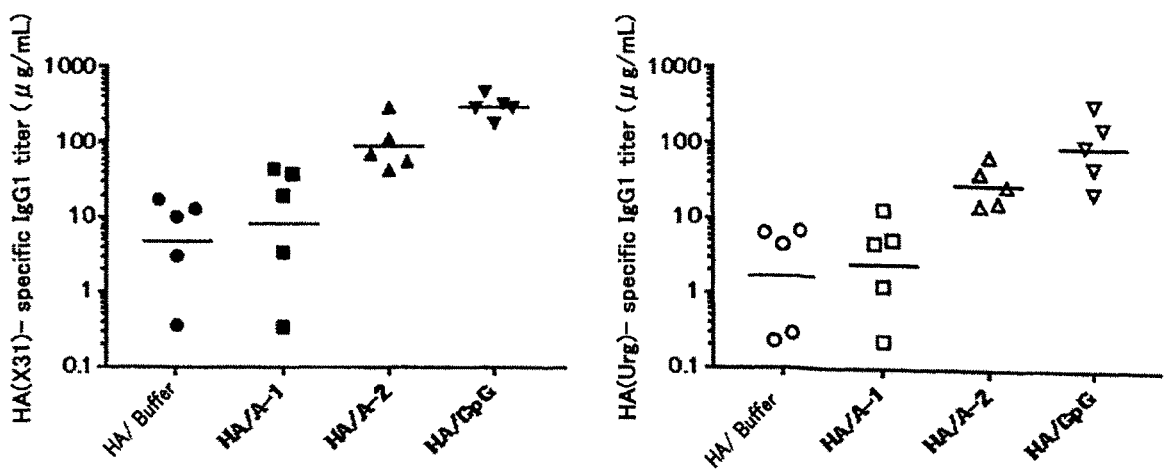

As shown in FIG. 8, the IgG1 titers against HA derived from strain X31 of all of the groups inoculated with the membrane fusion-type HA split vaccine with an adjuvant were significantly higher than that of the group inoculated with the membrane fusion-type HA split vaccine without adjuvant. Among the groups, the group administered with CpG-ODN1760/Freund's incomplete adjuvant (CpG/IFA) induced the highest IgG1 titer against HA derived from strain X31. Furthermore, for HA derived from Urg, exactly similar results of the reactivity were observed. Thus, these results show the induction of cross-reactive antibodies by the inoculation with the composition of the present application.

Figure 9:
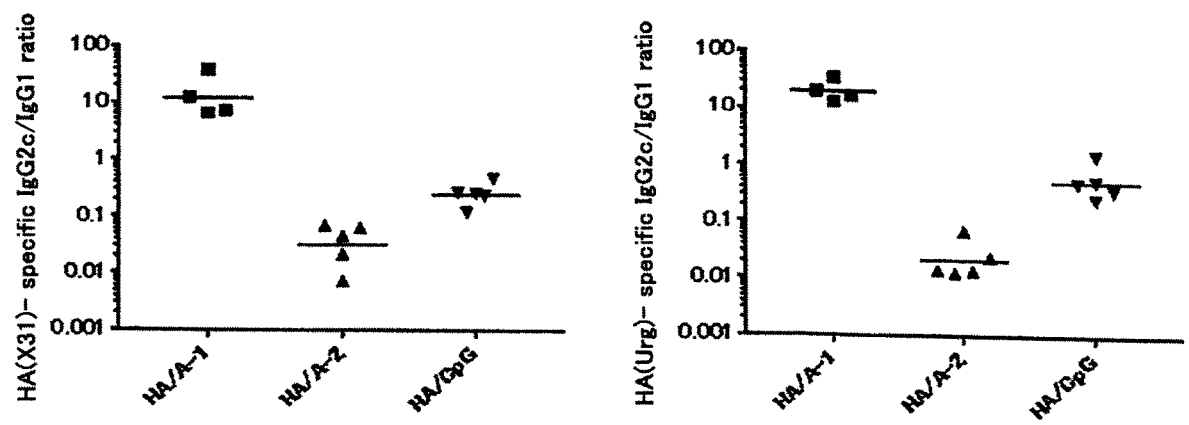

As shown in FIG. 9, the anti-HA derived from strain X31 IgG2c/IgG1 antibody ratio of A-1-administered group was higher than that of the group administered with CpG-ODN1760/Freund's incomplete adjuvant (CpG/IFA). Furthermore, for HA derived from Urg, exactly similar results of the anti-HA IgG2c/IgG1 antibody ratio were observed. Thus, these results show the induction of cross-reactive antibodies, which is highly effective in protection against infection, by the inoculation with the composition of the present application.

Figure 10:
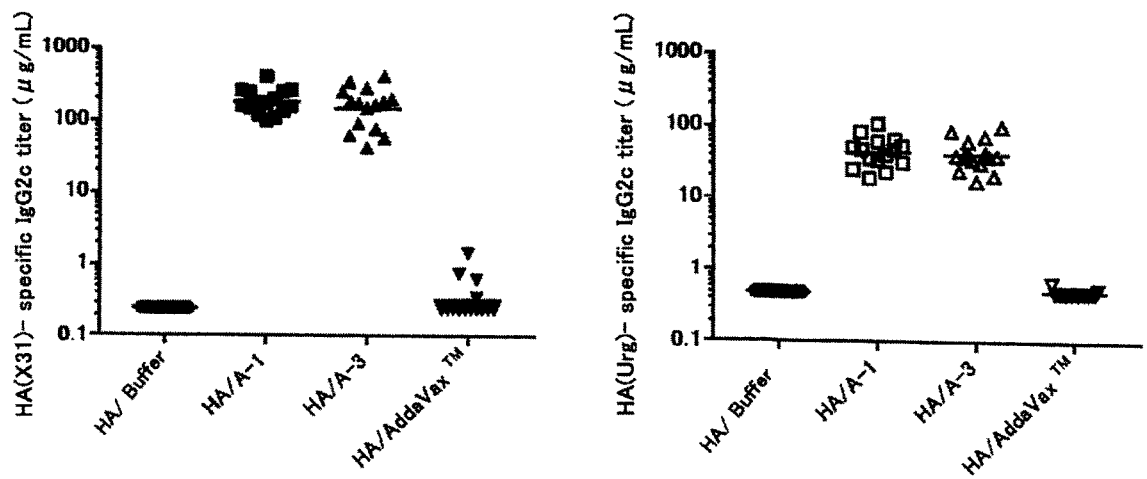

As shown in FIG. 10, the IgG2c titers against HA derived from strain X31 of all of the groups inoculated with the membrane fusion-type HA split vaccine with an adjuvant were significantly higher than that of the group inoculated with the membrane fusion-type HA split vaccine without adjuvant. The IgG2c titer against HA derived from strain X31 of A-1-administered group and A-3-administered group was higher than that of AddaVax adjuvant-administered group. Furthermore, for HA derived from Urg, exactly similar results of the reactivity were observed. Thus, these results show the induction of cross-reactive IgG2 antibodies, which is highly effective in protection against infection, by the inoculation with the composition of the present application.

Figure 11:
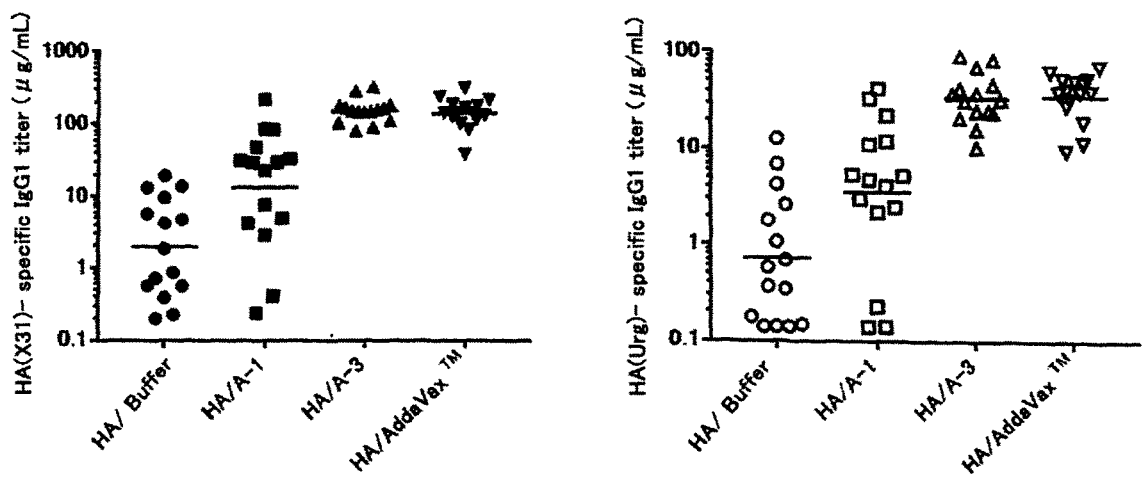

As shown in FIG. 11, the IgG1 titers against HA derived from strain X31 of all of the groups inoculated with the membrane fusion-type HA split vaccine with an adjuvant were significantly higher than that of the group inoculated with the membrane fusion-type HA split vaccine without adjuvant. Among the groups, A-3-administered group and AddaVax-administered group induced the highest IgG1 titer against HA derived from strain X31. Furthermore, for HA derived from Urg, exactly similar results of the reactivity were observed. Thus, these results show the induction of cross-reactive antibodies by the inoculation with the composition of the present application.

Figure 12:
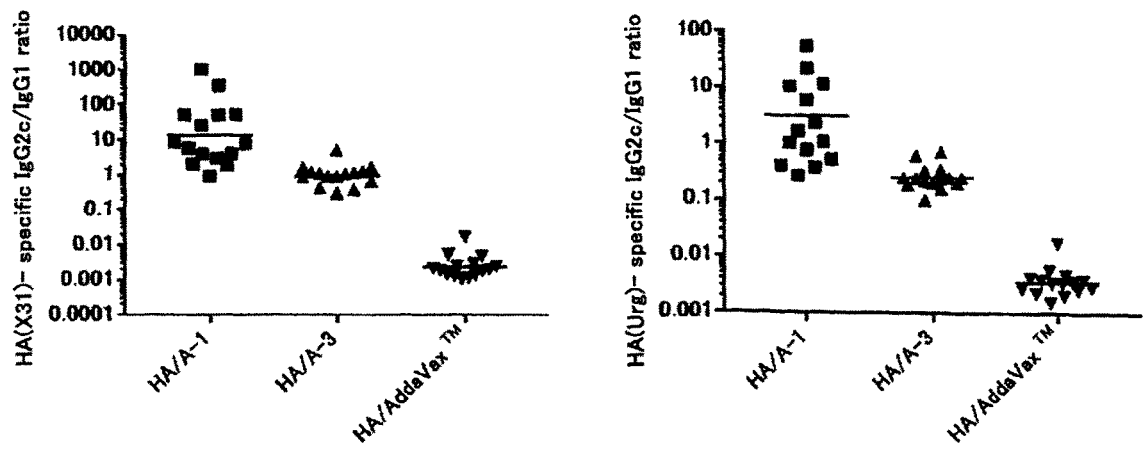

As shown in FIG. 12, the anti-HA derived from strain X31 IgG2c/IgG1 antibody ratios of A-1-administered group and A-3-administered group were higher than that of AddaVax adjuvant-administered group. Furthermore, for HA derived from Urg, exactly similar results of the anti-HA IgG2c/IgG1 antibody ratio were observed. Thus, these results show the induction of cross-reactive antibodies, which is highly effective in protection against infection, by the inoculation with the composition of the present application.

4. Cross-Protection Against Antigenic Variant

Three weeks after the booster, another H3N2 influenza virus (A/Guizhou/54/89) having different antigenicity from the vaccine strain was intranasally administered at 5 mouse lethal dose 50 (five times the amount of virus lethal to 50% of mice) under anesthesia. Mice were weighed and observed daily for 14 days from the viral infection to study the change in body weight and the survival rate. The humane endpoint was set at 25% body weight loss.

Figure 13:
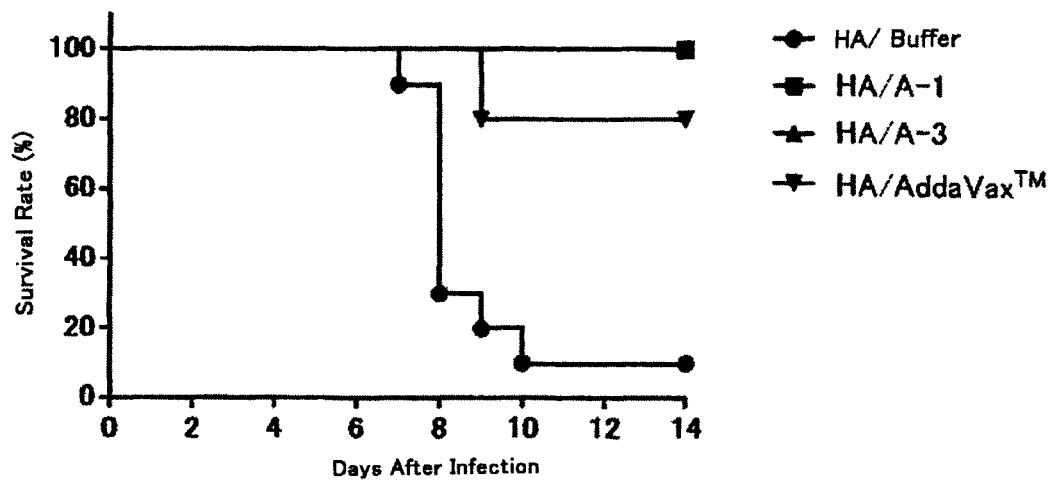

As shown in FIG. 13, regarding all of the mice groups inoculated with the membrane fusion-type HA split vaccine with an adjuvant, the decrease in the survival rates were significantly curbed on and after the seven day after the infection with the other H3N2 influenza virus of different antigenicity. Among them, A-1-administered group and A-3-administered group showed 100% survivals and the highest effects of protection against infection.

Figure 14:
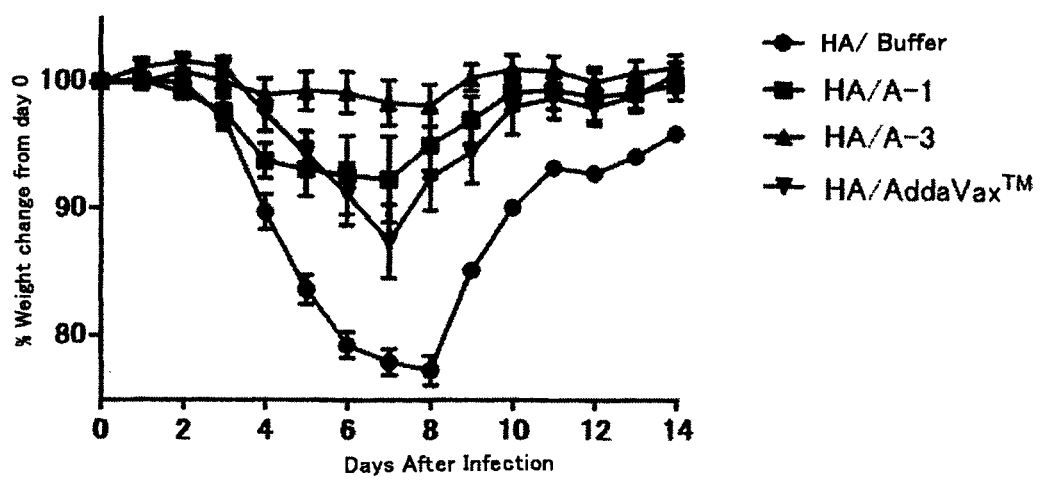
Figure 15:
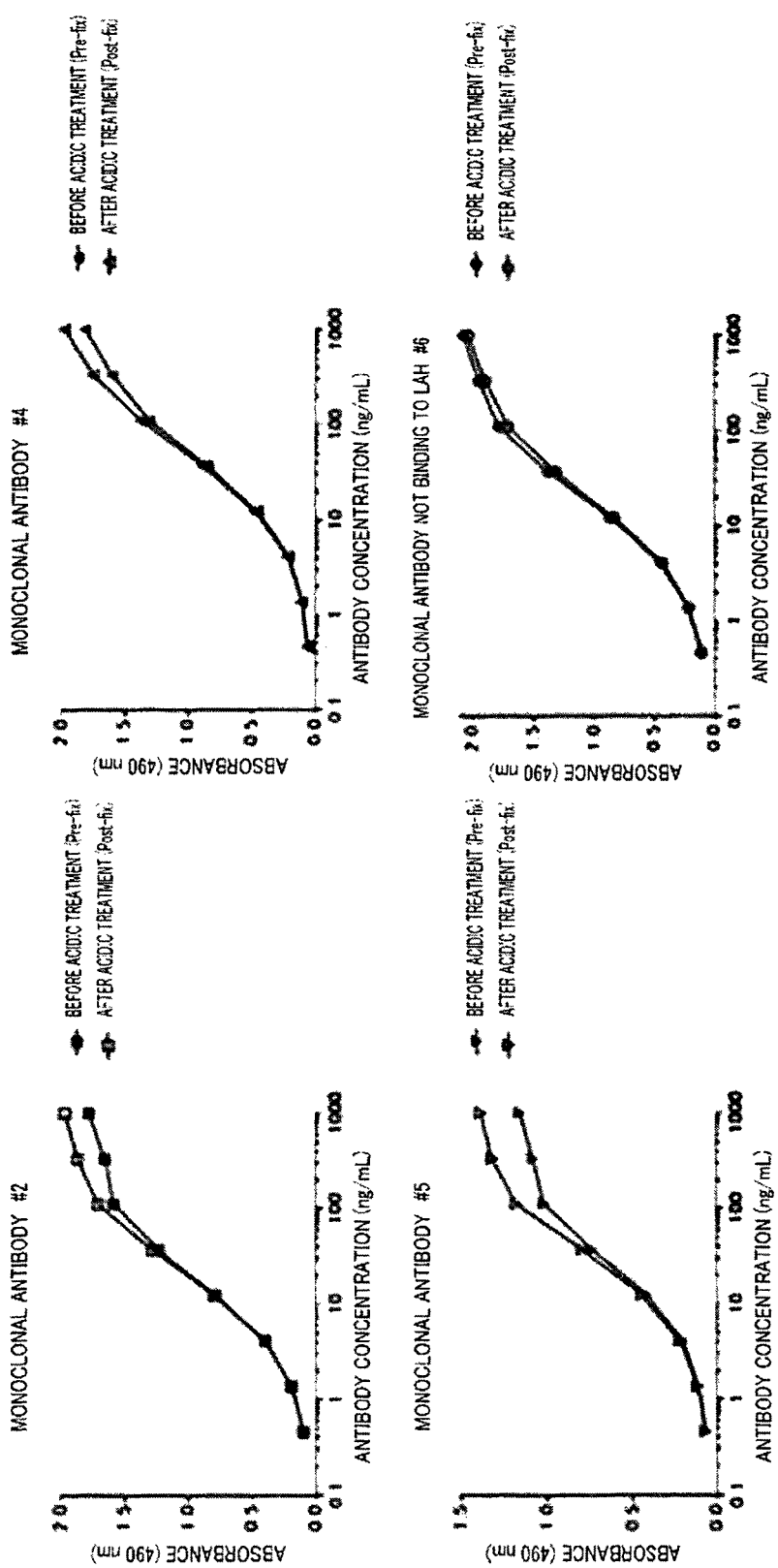

As shown in FIG. 14, regarding all of the mice groups inoculated with the membrane fusion-type HA split vaccine with an adjuvant, the body weight losses due to the infection with the other H3N2 influenza virus of different antigenicity were suppressed. Among the groups, A-3-administered group showed a higher effect of suppressing the body weight loss than that of AddaVax adjuvant-administered group.

5. Administration of the Composition of the Present Invention, Comprising an Influenza HA Split Vaccine and a Compound That Enhances the Physiological Activity of TLR7

The membrane fusion-type HA split vaccine derived from strain PR8 of H1N1 influenza virus (10 µg) and: phosphate buffered saline; A-1 containing 50 µg of TLR7 agonist (Compound A); A-3 containing 10 µg of TLR7 agonist (Compound A); or AddaVax adjuvant (InvivoGen) whose volume was equal to the liquid of membrane fusion-type HA split vaccine derived from strain PR8, were mixed to give each composition. C57BL/6 mice (female, 6 to 12 week old) were inoculated intradermally in the thighs or intramuscularly in the thighs (50 µl into each thigh, 100 µl in total) with the above composition. After 3 weeks, the same mice were boosted with the same antigen and under the same conditions. Two weeks after the booster, blood was drawn, from which serum was collected.

6. Measurement by ELISA

The concentration of the anti-HA antibody in the sera of the mice was measured by ELISA in the following manner. A recombinant HA protein (strain PR8 or A/Narita/1/09 of H1N1 influenza virus) was dissolved in phosphate buffered saline (pH 7.3) at 10 µg/ml, and added to 96-well plates by 100 µl each. After standing overnight at 4° C., each well was washed three times with phosphate buffered saline, and 150 µl of phosphate buffered saline containing 1 v/v % bovine serum albumin was added. After standing at room temperature for two hours, each well was washed three times with phosphate buffered saline. Then, 100 µl of a mouse serum serially diluted with phosphate buffer containing 0.05 v/v % of Tween 20 and 1 v/v % bovine serum albumin, and 100 µl of a standard monoclonal antibody of known concentration (H1; clone name F2) were added to each well. After standing at room temperature for two hours, each well was washed three times with phosphate buffered saline (containing 0.05 v/v % of Tween 20), and 100 µl of a peroxidase-labeled anti-mouse IgG1 antibody or IgG2c antibody (Southern Biotech) diluted with phosphate buffered saline containing 0.05 v/v % Tween 20 and 1 v/v % bovine serum albumin was added to each well. After standing at room temperature for two hours, each well was washed three times with phosphate buffered saline (containing 0.05 v/v % of Tween 20). Then, 30 mg of o-phenylendiamine tablet (Sigma) and 24 µl of 30% hydrogen peroxide solution (30% w/w; Sigma) were added to 60 ml of citrate buffer (pH 5.0) as a substrate, and 100 µl of the resultant was added to each well. After the color development, 50 µl of 1 mol/L sulfuric acid (Wako Pure Chemical Industries, Ltd.) was added to stop the reaction, and an absorbance value at 490 nm was measured using a Microplate Reader 450 (Biorad).

Figure 17:
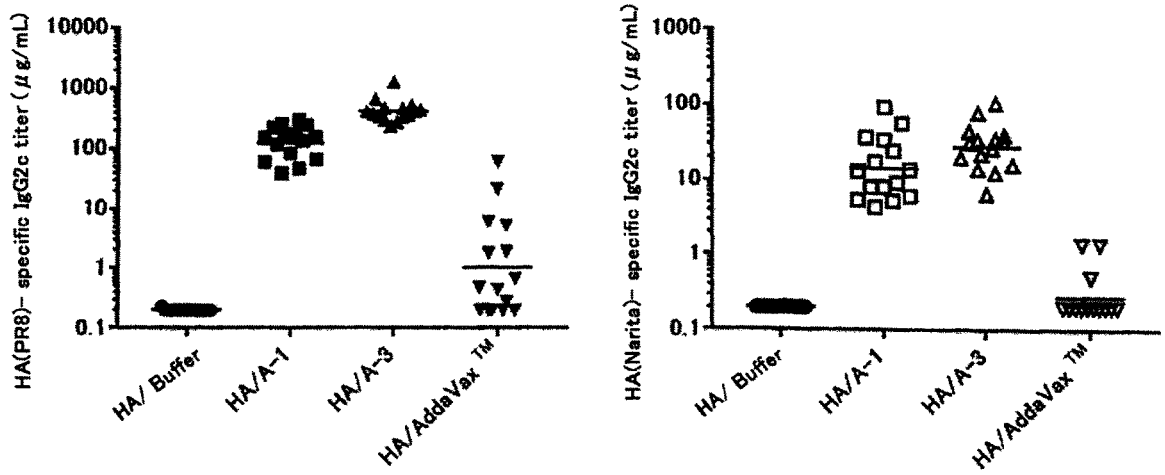

As shown in FIG. 17, the IgG2c titers against HA derived from strain PR8 of all of the groups inoculated with the membrane fusion-type HA split vaccine with an adjuvant were significantly higher than that of the group inoculated with the membrane fusion-type HA split vaccine without adjuvant. The IgG2c titer against HA derived from strain PR8 of A-1-administered group was higher than that of AddaVax adjuvant-administered group. Among the groups, A-3-administered group induced the highest IgG2c titer against HA derived from strain PR8. Furthermore, for HA derived from A/Narita/1/09, exactly similar results of the reactivity were observed. Thus, these results show the induction of cross-reactive IgG2 antibodies, which is highly effective in protection against infection, by the inoculation with the composition of the present application.

Figure 18:
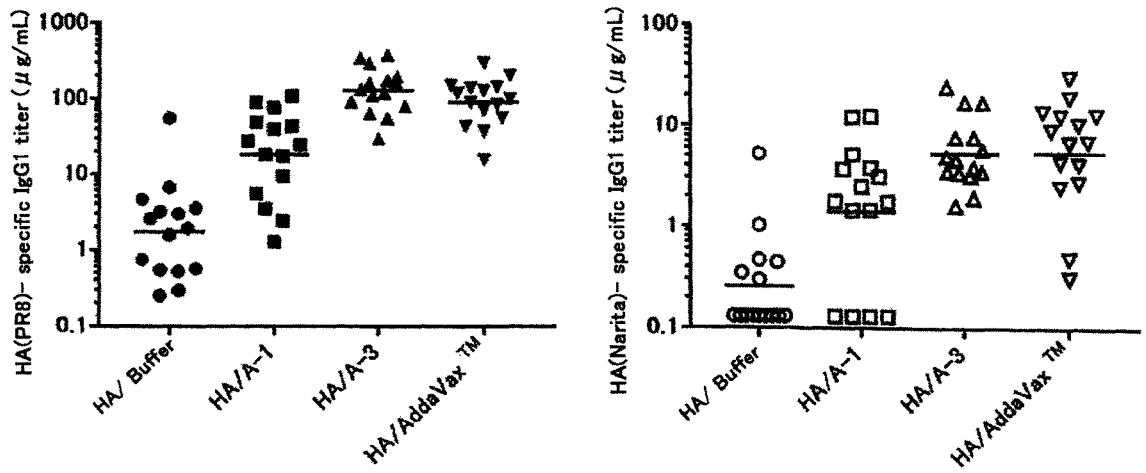

As shown in FIG. 18, the IgG1 titers against HA derived from strain PR8 of all of the groups inoculated with the membrane fusion-type HA split vaccine with an adjuvant were significantly higher than that of the group inoculated with the membrane fusion-type HA split vaccine without adjuvant. Among the groups, A-3-administered group induced the highest IgG1 titer against HA derived from strain PR8. Furthermore, for HA derived from A/Narita/1/09, exactly similar results of the reactivity were observed. Thus, these results show the induction of cross-reactive antibodies by the inoculation with the composition of the present application.

Figure 19:
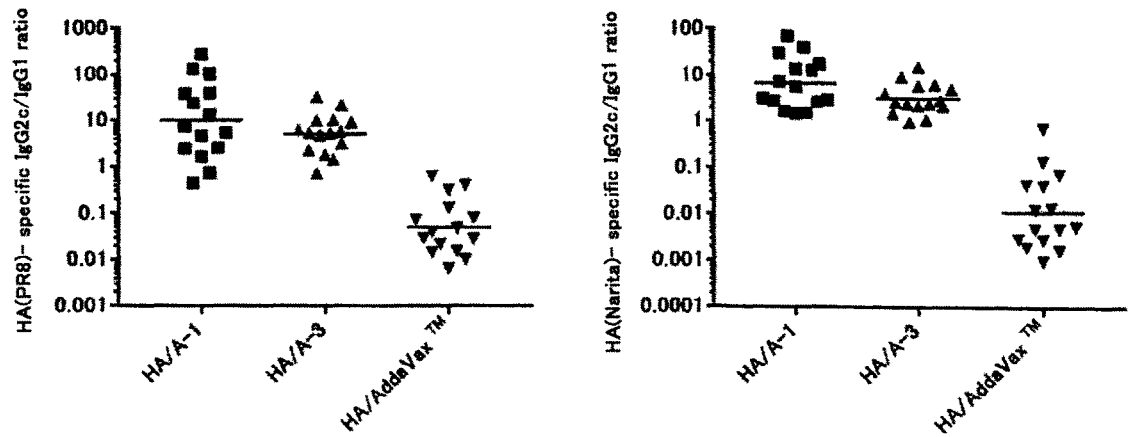

As shown in FIG. 19, the anti-HA derived from strain PR8 IgG2c/IgG1 antibody ratios of A-1-administered group and A-3-administered group were higher than that of AddaVax adjuvant-administered group. Furthermore, for HA derived from A/Narita/1/09, exactly similar results of the anti-HA IgG2c/IgG1 antibody ratio were observed. Thus, these results show the induction of cross-reactive antibodies, which is highly effective in protection against infection, by the inoculation with the composition of the present application.

7. Cross-Protection Against Antigenic Variant

Four weeks after the booster, another H1N1 influenza virus (A/Narita/1/09) having different antigenicity from the vaccine strain was intranasally administered at 5 mouse lethal dose 50 (five times the amount of virus lethal to 50% of mice) under anesthesia. Mice were weighed and observed daily for 14 days from the viral infection to study the change in body weight and the survival rate. The humane endpoint was set at 25% body weight loss.

Figure 20:
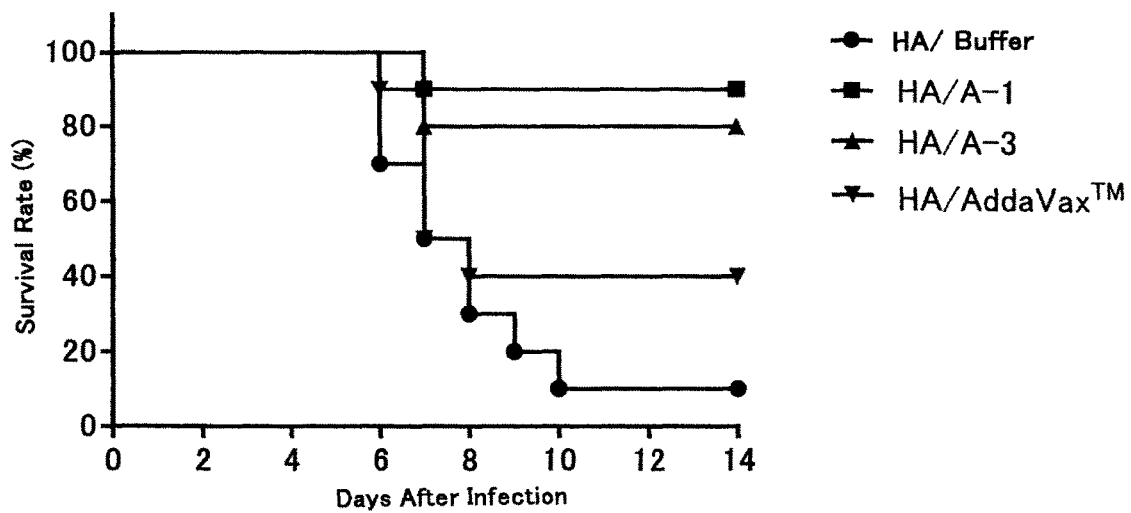

As shown in FIG. 20, regarding the mice groups inoculated with the membrane fusion-type HA split vaccine with A-1 adjuvant or A-3 adjuvant, the decrease in the survival rates were significantly curbed on and after the seven day after the infection with the other H1N1 influenza virus of different antigenicity, which showed a strong infection protection effect.

Figure 21:
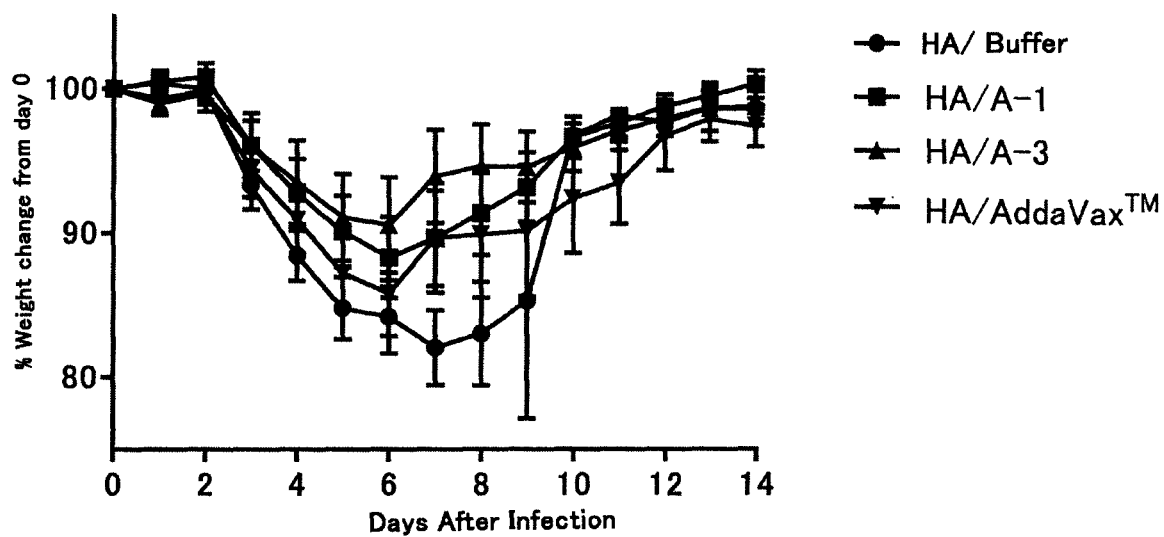

As shown in FIG. 21, regarding all of the mice group inoculated with the membrane fusion-type HA split vaccine with an adjuvant, the body weight losses due to the infection with the other H1N1 influenza virus of different antigenicity were suppressed. Among the groups, A-1-administered group and A-3-administered group showed higher effects of suppressing the body weight loss than that of AddaVax adjuvant-administered group.

Example 3: Influence of Order of Formalin Treatment on Binding Capacity of Antibody and Antibody Inducibility

1. Preparation of Formalin-Pretreated HA Split Vaccine

To particles of H3N2 influenza virus (strain X31) suspended in phosphate buffered saline, Tween 80 was added and suspended in a final concentration of 0.1 v/v %. Diethyl ether was added and suspended, and the suspension was left stand until an aqueous layer and a diethyl ether layer were completely separated, and then the diethyl ether layer was removed.

After repeating this ether extraction, diethyl ether remaining in the recovered aqueous layer was distilled off at normal pressure. Further, formalin was added at a final concentration of 0.05 v/v %, and the mixture was left stand for several days to obtain a formalin-pretreated HA split vaccine.

2. Acidic Treatment of Formalin-Pretreated HA Split Vaccine

The formalin-pretreated HA split vaccine was suspended in phosphate buffered saline, and then an acidic treatment was performed by adding 0.15 M citrate buffer (pH 3.5) to bring the pH to 5.0. After standing at room temperature for 30 minutes, 1 M Tris buffer (pH 8.0) was added so that the pH was returned to 7.3. Thereafter, centrifugation was performed.

3. Binding Capacity of Antibody to LAH Epitope

Figure 6:
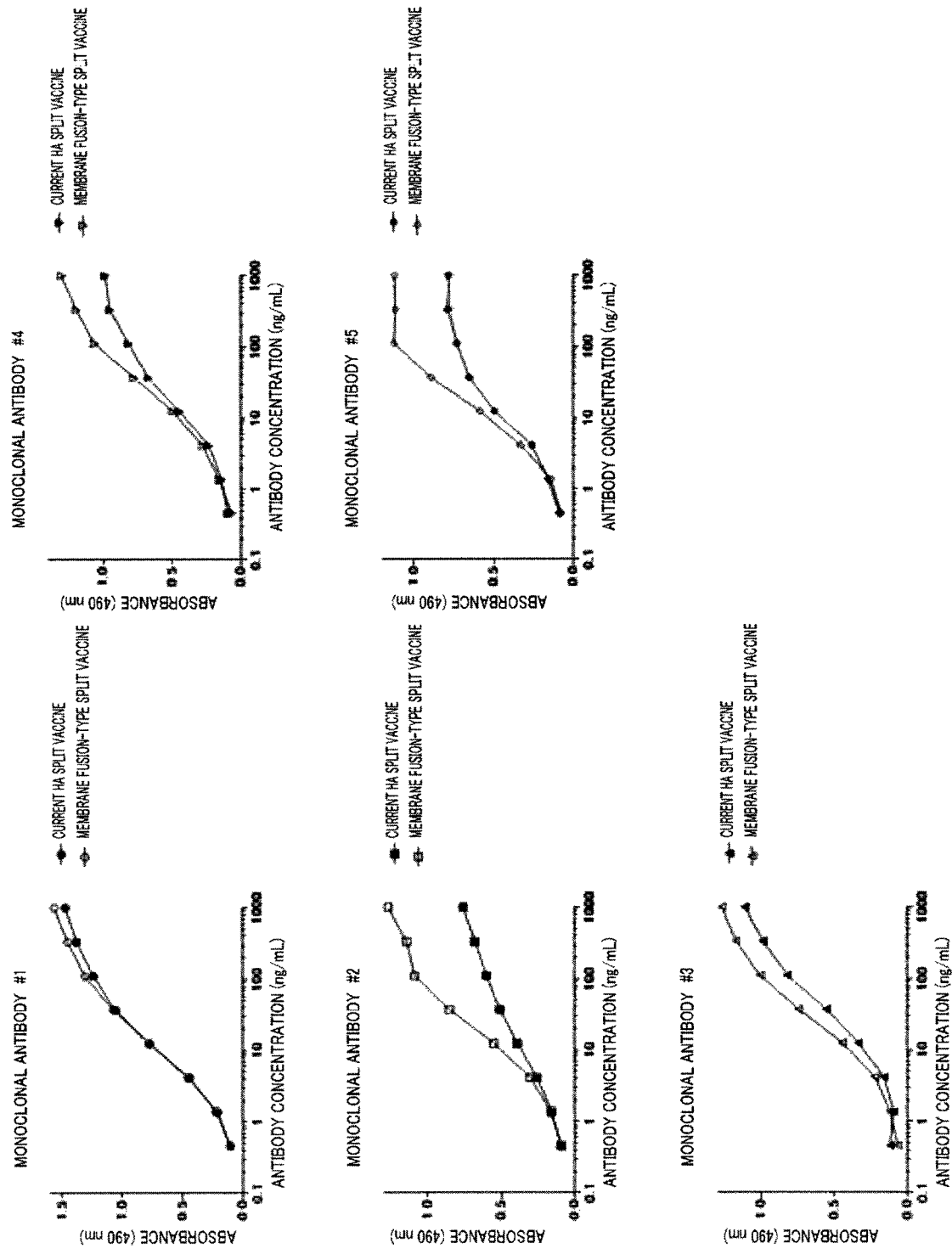

The binding capacity of the antibody to the LAH epitope was measured in the same manner as described in Example 1, and the change in the binding capacity was calculated. Here, the same antibodies as #2, #4 and #5 shown in FIG. 6 were used as the monoclonal antibodies, and the monoclonal antibody #6 which binds to the HA head region was used as a control.

4. Measurement of Titer of Anti-LAH Antibody by ELISA

4-1. Inoculation of H3N2 Influenza Vaccine

BALB/c mice (female, 6 to 12 weeks old) were intraperitoneally inoculated with the current H3N2 HA split vaccine or the membrane fusion-type HA split vaccine (10 μg vaccine+10 v/v % AddaVax adjuvant (InvivoGen) dissolved in phosphate buffered saline to a liquid volume of 200 μl). At least 12 days after the inoculation, blood was collected from the mice inoculated with the vaccines, from which sera were collected.

4-2. Measurement by ELISA

The titer of the anti-LAH antibody was measured in the same manner as described in 3-2 in the above Example 1.

As shown in FIG. 15, the LAH binding monoclonal antibody bound to the vaccine (Post-fix) that had undergone the formalin treatment after the acidic treatment in the process of preparing the membrane fusion-type HA split vaccine more strongly than to the vaccine (Pre-fix) that had undergone the formalin treatment prior to the acidic treatment. The results indicate that when to perform the formalin treatment has influence on the enhancement of the binding capacity of the antibody to the LAH epitope obtained through the acidic treatment of the HA split vaccine, and that the formalin treatment is desirably performed after the acidic treatment. In FIGS. 15 and 16, a vaccine obtained by subjecting the HA split vaccine to the acidic treatment after the formalin treatment in the same manner as described in Example 3 is referred to as "a membrane fusion-type split vaccine (Pre-fix)." Further, according to the procedure of Example 1, a vaccine obtained by subjecting the HA split vaccine to the formalin treatment after the acidic treatment in the same manner as described in Example 1 is referred to as "a membrane fusion-type split vaccine (Post-fix)."

Figure 16:
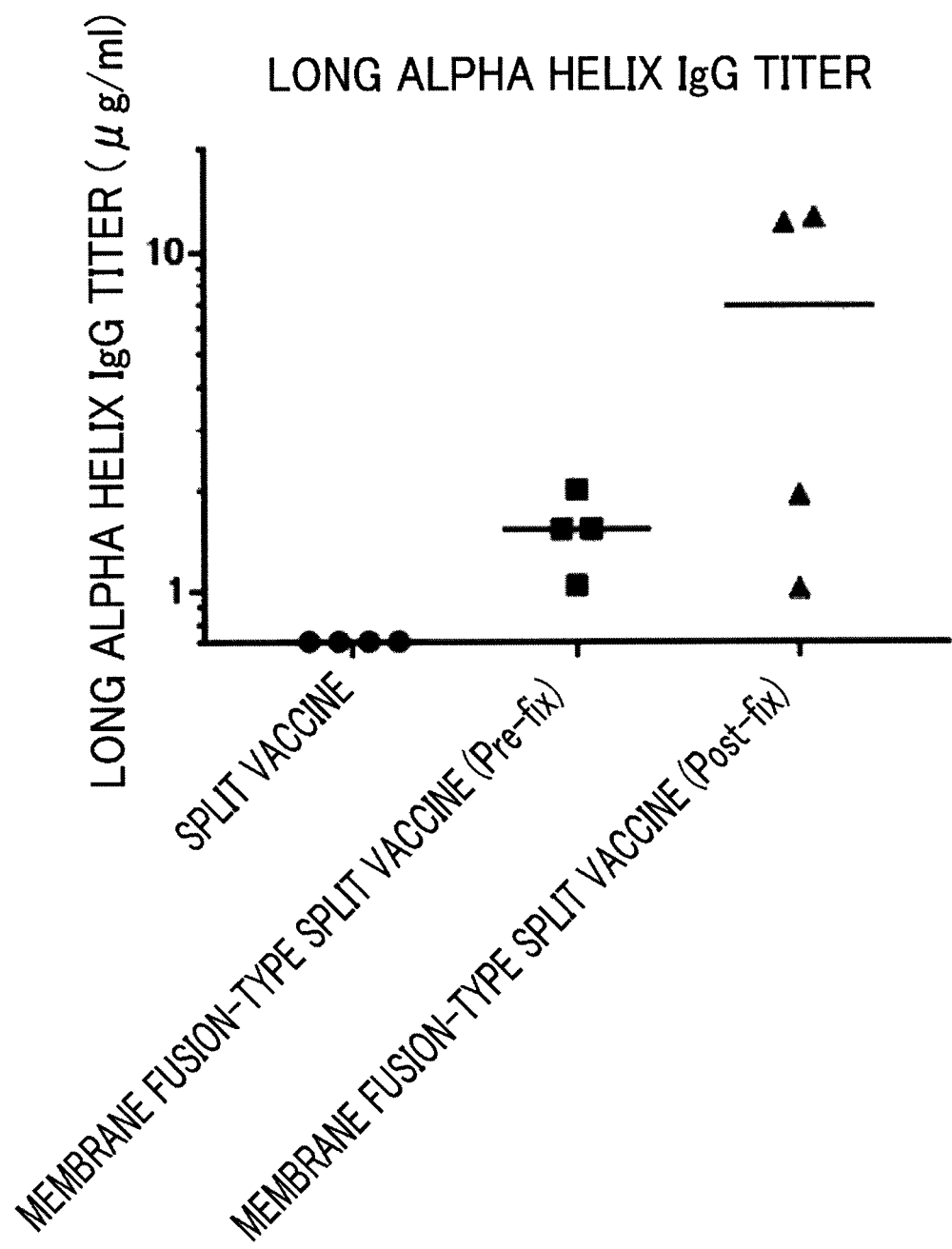

As shown in FIG. 16, the titer of the anti-LAH antibody in the sera of the BALB/c mice intraperitoneally inoculated with the membrane fusion-type HA split vaccine was higher than the titer of the anti-LAH antibody in the sera of the BALB/c mice intraperitoneally inoculated with the current HA split vaccine. Furthermore, the membrane fusion-type HA split vaccine (Post-fix) exhibited higher titer of the anti-LAH antibody than the membrane fusion-type split vaccine (Pre-fix).

INDUSTRIAL APPLICABILITY

The present invention can be used in the field of development or production of influenza vaccines.

SEQUENCE LISTING FREE TEXT

SEQ ID NO: 1, 2: Synthetic Peptide

The invention claimed is:

1. A composition comprising the following (1) and (2);
   (1) a universal influenza vaccine antigen; and
   (2) a vaccine adjuvant;
   wherein the vaccine adjuvant is a substance which enhances the physiological activity of TLR7, which is selected from the group consisting of:
   (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;
   (4E,8E,12E,16E,20E)-1-(4-{4-[(2-amino-4-{[(2S)-1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one;
   (4E,8E,12E,16E,20E)-1-(4-{4-[(2-amino-4-{[(2S)-1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one;
   4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; and
   4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide; or
   a pharmaceutically acceptable salt thereof.

2. The composition according to claim 1, wherein the universal influenza vaccine antigen is an influenza HA split vaccine antigen which produces an antibody that binds to a LAH of a HA stem region.

3. The composition according to claim 2, wherein the influenza HA split vaccine antigen has a HA stem region exposed outside.

4. The composition according to claim 1, wherein the universal influenza vaccine antigen is an influenza HA split vaccine antigen wherein the HA stem region, which is exposed outside, enhances the antigenicity of the LAH of the HA stem region, and the influenza HA split vaccine is capable of producing an antibody that binds to the LAH of the HA stem region.

5. The composition according to claim 1, wherein the universal influenza vaccine antigen is produced by subjecting an influenza HA split vaccine to an acidic treatment.

6. The composition according to claim 1, wherein the universal influenza vaccine antigen is produced by a production process including: subjecting an influenza HA split vaccine to an acidic treatment; and thereafter, subjecting the influenza HA split vaccine to a formalin treatment.

7. The composition according to claim 1, wherein the substance which enhances the physiological activity of TLR7 is:
   (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide; or
   4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; or
   a pharmaceutically acceptable salt thereof.

8. An influenza vaccine comprising the composition according to claim 1.

9. A kit comprising a universal influenza vaccine antigen, and a vaccine adjuvant;
   wherein the vaccine adjuvant is a substance which enhances the physiological activity of TLR7, which is selected from the group consisting of:
   (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide;
   (4E,8E,12E,16E,20E)-1-(4-{4-[(2-amino-4-{[(2S)-1-hydroxypentan-2-yl]amino}-6-methylpyrimidin-5-yl)methyl]-3-methoxybenzyl}piperazin-1-yl)-4,8,12,17,21,25-hexamethylhexacosa-4,8,12,16,20,24-hexaen-1-one;
   (4E,8E,12E,16E,20E)-1-(4-{4-[(2-amino-4-{[(2S)-1-hydroxypentan-2-yl]amino}-6-methylpyrimidin-5-yl)methyl]-3-methoxybenzoyl}piperazin-1-yl)-4,8,12,17,21,25-hexamethylhexacosa-4,8,12,16,20,24-hexaen-1-one;
   4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl]amino}ethyl)-3-methoxybenzamide; and
   4-[(2-amino-4-{[(2S)-1-hydroxypentan-2-yl]amino}-6-methylpyrimidin-5-yl)methyl]-N-(2-{[(4E,8E,12E,16E,20E)-4,8,12,17,21,25-hexamethylhexacosa-4,8,12,16,20,24-hexaenoyl](methyl)amino}ethyl)-3-methoxybenzamide; or
   a pharmaceutically acceptable salt thereof.

10. The composition according to claim 1, wherein the universal influenza vaccine antigen is produced by subjecting an influenza HA split vaccine which has not undergone a formalin treatment to an acidic treatment.

11. The composition according to claim 1, wherein the universal influenza vaccine antigen is produced by subjecting an influenza HA split vaccine of a single HA subtype to an acidic treatment.

12. The composition of according to claim 1, wherein the universal influenza vaccine antigen is a vaccine antigen comprising two or more kinds of influenza HA split vaccine antigens each of which is produced by subjecting an influenza HA split vaccine of a single HA subtype to an acidic treatment.

13. The composition according to claim 1, wherein the substance which enhances the physiological activity of TLR7 is:
   (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide; or
   a pharmaceutically acceptable salt thereof.

14. The composition according to claim 1, wherein the universal influenza vaccine antigen is an influenza HA split vaccine antigen which produces an antibody that binds to a LAH of a HA stem region, and the substance which enhances the physiological activity of TLR7 is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide or a pharmaceutically acceptable salt thereof.

15. The composition according to claim 1, wherein the universal influenza vaccine antigen is produced by subjecting an influenza HA split vaccine to an acidic treatment, and the substance which enhances the physiological activity of TLR7 is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide or a pharmaceutically acceptable salt thereof.

16. The influenza vaccine according to claim 8, wherein the universal influenza vaccine antigen is an influenza HA split vaccine antigen which produces an antibody that binds to a LAH of a HA stem region, and the substance which enhances the physiological activity of TLR7 is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide or a pharmaceutically acceptable salt thereof.

17. The influenza vaccine according to claim 8, wherein the universal influenza vaccine antigen is produced by subjecting an influenza HA split vaccine to an acidic treatment, and the substance which enhances the physiological activity of TLR7 is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide or a pharmaceutically acceptable salt thereof.

18. The kit according to claim 9, wherein the universal influenza vaccine antigen is an influenza HA split vaccine antigen which produces an antibody that binds to a LAH of a HA stem region, and the substance which enhances the physiological activity of TLR7 is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide or a pharmaceutically acceptable salt thereof.

19. The kit according to claim 9, wherein the universal influenza vaccine antigen is produced by subjecting an influenza HA split vaccine to an acidic treatment, and the substance which enhances the physiological activity of TLR7 is (4E,8E,12E,16E,20E)-N-{2-[{4-[(2-amino-4-{[(3S)-1-hydroxyhexan-3-yl]amino}-6-methylpyrimidin-5-yl)methyl]benzyl}(methyl)amino]ethyl}-4,8,12,17,21,25-hexamethylhexacosa-4,8,12,16,20,24-hexaenamide or a pharmaceutically acceptable salt thereof.

* * * * *

UNITED STATES PATENT AND TRADEMARK OFFICE
CERTIFICATE OF CORRECTION

PATENT NO. : 12,059,462 B2
APPLICATION NO. : 17/262021
DATED : August 13, 2024
INVENTOR(S) : Yoshimasa Takahashi et al.

It is certified that error appears in the above-identified patent and that said Letters Patent is hereby corrected as shown below:

In the Claims

In Column 40 Line 41 In Claim 12, after "composition" delete "of".

Signed and Sealed this
Twenty-sixth Day of November, 2024

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 64
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 1

Arg Ile Gln Asp Leu Glu Lys Tyr Val Glu Asp Thr Lys Ile Asp Leu
1               5                   10                  15

Trp Ser Tyr Asn Ala Glu Leu Leu Val Ala Leu Glu Asn Gln His Thr
            20                  25                  30

Ile Asp Leu Thr Asp Ser Glu Met Asn Lys Leu Phe Glu Lys Thr Arg
        35                  40                  45

Arg Gln Leu Arg Glu Asn Ala Asp Tyr Lys Asp Asp Asp Lys Cys
    50                  55                  60

<210> SEQ ID NO 2
<211> LENGTH: 64
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION

<400> SEQUENCE: 2

Arg Ile Glu Asn Leu Asn Lys Lys Val Asp Asp Gly Phe Leu Asp Ile
1               5                   10                  15

Trp Thr Tyr Asn Ala Glu Leu Leu Val Leu Leu Glu Asn Glu Arg Thr
            20                  25                  30

Leu Asp Tyr His Asp Ser Asn Val Lys Asn Leu Tyr Glu Lys Val Arg
        35                  40                  45

Ser Gln Leu Lys Asn Asn Ala Asp Tyr Lys Asp Asp Asp Lys Cys
    50                  55                  60
```